(12) United States Patent
Calasso et al.

(10) Patent No.: US 10,307,533 B2
(45) Date of Patent: Jun. 4, 2019

(54) MEDICAL FLUID-FLOW REGULATING DEVICES WITH BLOCKING UNIT

(71) Applicant: MEDIRIO S.A., Visp (CH)

(72) Inventors: Irio Giuseppe Calasso, Arth (CH); Einar Petersen, Maaloev (DK); Tobias Von Cappelen, Farum (DK); Klaus Dietrich, Altach (AT); Matteo De Donatis, Sion (CH)

(73) Assignee: Medirio S.A., Visp (CH)

( * ) Notice: Subject to any disclaimer, the term of this patent is extended or adjusted under 35 U.S.C. 154(b) by 302 days.

(21) Appl. No.: 15/253,952

(22) Filed: Sep. 1, 2016

(65) Prior Publication Data
US 2017/0056587 A1    Mar. 2, 2017

(30) Foreign Application Priority Data
Sep. 1, 2015 (EP) .................................. 15183406

(51) Int. Cl.
*A61M 5/168* (2006.01)
*A61M 5/142* (2006.01)
*A61M 5/14* (2006.01)
*A61M 39/22* (2006.01)

(52) U.S. Cl.
CPC ...... *A61M 5/16804* (2013.01); *A61M 5/1413* (2013.01); *A61M 5/14216* (2013.01); *A61M 5/14248* (2013.01); *A61M 5/16831* (2013.01); *A61M 2005/14268* (2013.01); *A61M 2039/226* (2013.01); *A61M 2205/18* (2013.01);
(Continued)

(58) Field of Classification Search
CPC .......... A61M 5/16804; A61M 5/16831; A61M 2005/16863
See application file for complete search history.

(56) References Cited

U.S. PATENT DOCUMENTS

| 8,523,803 B1 * | 9/2013 | Favreau ................ A61M 5/142 604/67 |
| 8,970,384 B2 * | 3/2015 | Yodfat .............. A61M 5/16831 340/573.1 |
| 2012/0245515 A1 | 9/2012 | Calasso et al. |

(Continued)

FOREIGN PATENT DOCUMENTS

| EP | 2617445 A1 | 7/2013 |
| EP | 2674177 A1 | 12/2013 |

(Continued)

*Primary Examiner* — Laura A Bouchelle
(74) *Attorney, Agent, or Firm* — Blank Rome LLP

(57) ABSTRACT

Medical fluid-flow regulating devices are provided. Such medical fluid-flow regulating devices typically include a rotor and a flow-regulator element engaged or engageable with each other via a coupling that below a torque and/or fluidic-pressure threshold value allows the flow-regulator element to move upon rotation of the rotor and thereby regulate fluid flow. The medical fluid-flow regulating devices also include a blocking unit that above the torque and/or fluidic-pressure threshold value irreversibly blocks the rotor or the flow-regulator element or the coupling between the rotor and the flow-regulator element resulting in irreversible inactivation of the medical fluid-flow regulating device. Systems incorporating such medical fluid-flow regulating devices are also provided. Methods for detecting inactivation of such devices are also provided.

16 Claims, 11 Drawing Sheets

(52) U.S. Cl.
CPC .................. *A61M 2205/332* (2013.01); *A61M 2205/3341* (2013.01)

(56) References Cited

U.S. PATENT DOCUMENTS

2013/0181538 A1    7/2013   Calasso
2013/0338592 A1   12/2013   Calasso

FOREIGN PATENT DOCUMENTS

| EP | 2764881 A1 | 8/2014 |
| EP | 2910263 A1 | 8/2015 |
| WO | 2010072010 A2 | 7/2010 |

\* cited by examiner

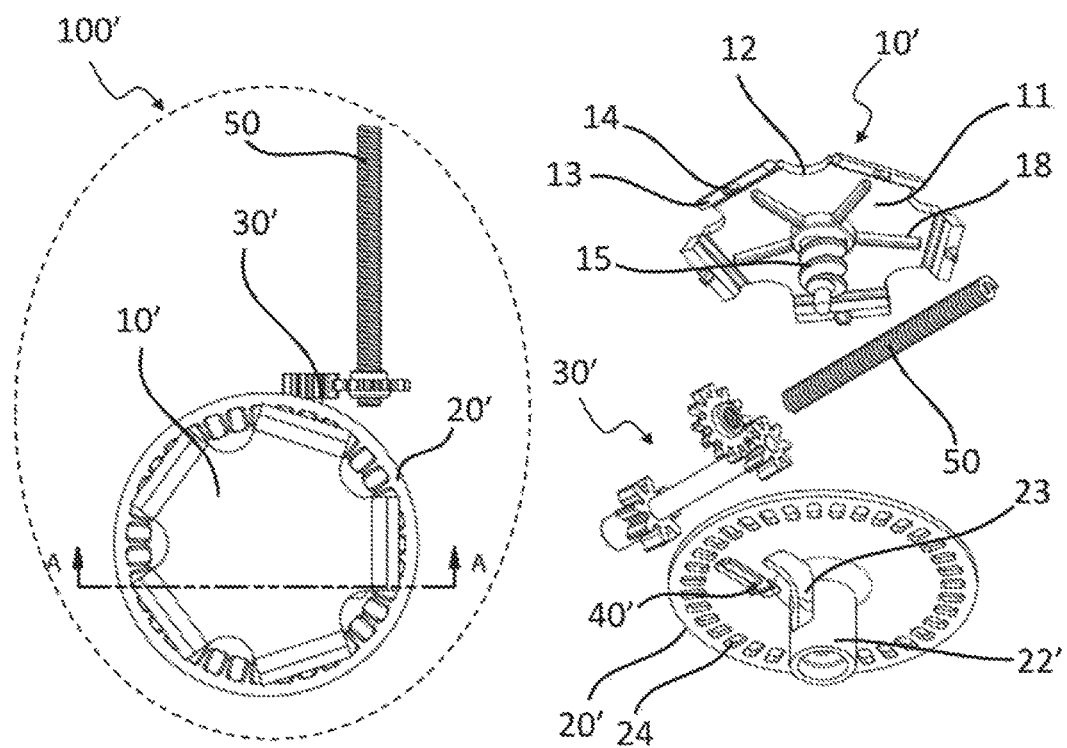
FIG. 2a
FIG. 2b
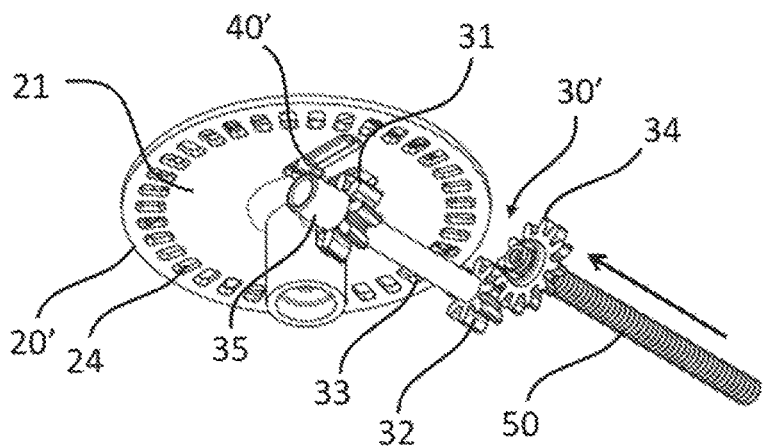
FIG. 2c

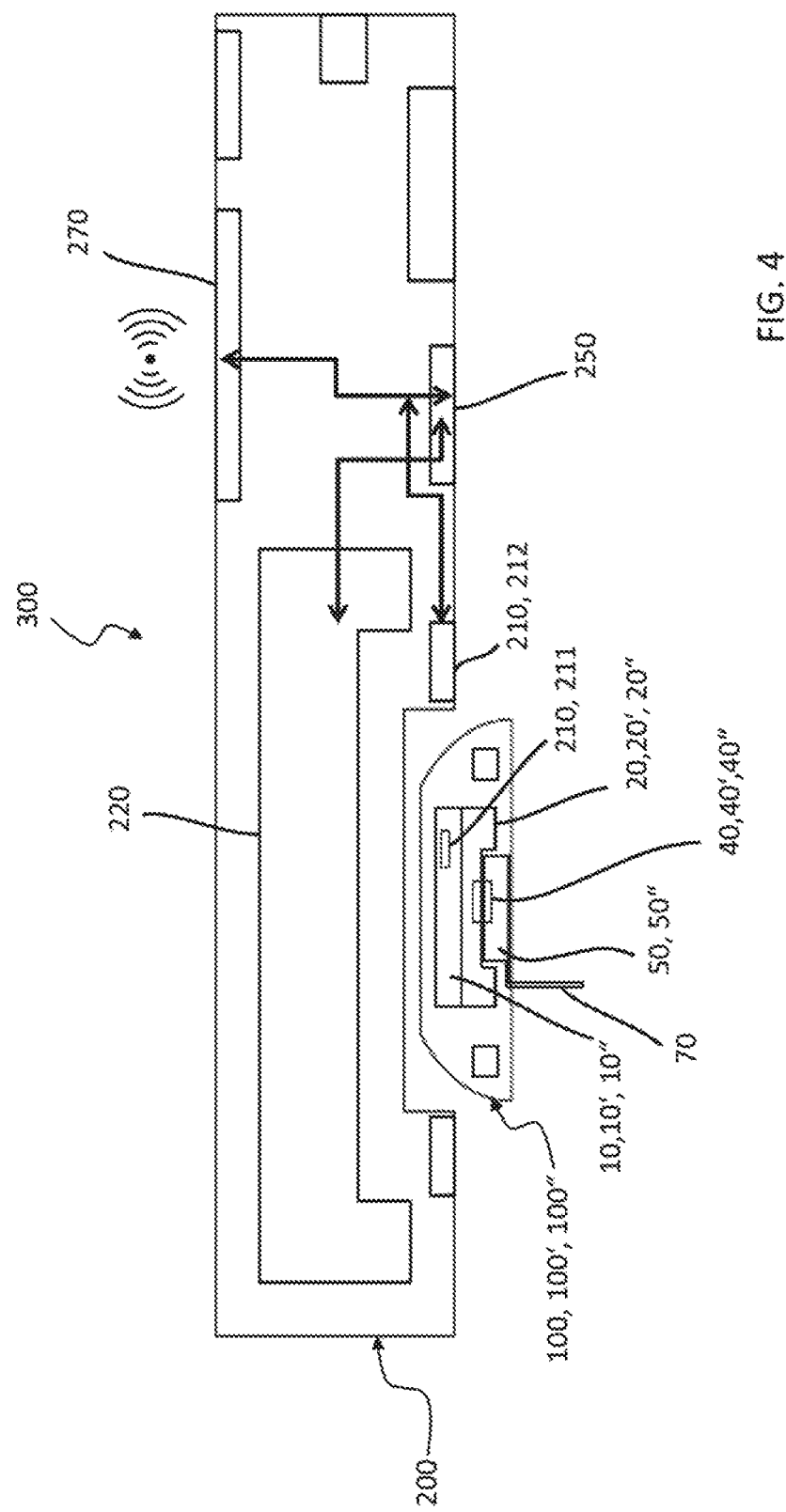

MEDICAL FLUID-FLOW REGULATING DEVICES WITH BLOCKING UNIT

CROSS REFERENCE TO RELATED APPLICATION

This application claims priority to and benefit of European Patent Application No. 15183406.6 filed Sep. 1, 2015, the contents of which are incorporated by reference in their entirety.

FIELD OF THE INVENTION

The present invention is directed to medical fluid-flow regulating devices, and systems and to methods that prevent use of medical fluid-flow regulating devices in the event that something occurs to prevent proper operation.

BACKGROUND OF THE INVENTION

Some medical conditions require regular dosage or continuous infusion of medicaments. These medicaments are often provided as liquid solutions to be infused, e.g. transdermally. Diabetic patients, for example, may require insulin. In the attempt to make the life of these patients easier, infusion devices have been developed. Infusion devices known in the art typically comprise simple injection pen-like devices or complex pump devices, and use mechanical or electro-mechanical pumping to deliver the medicament to a patient through the skin. The injection pen-like devices require the patient to make a new injection every time, they are not discreet and are associated with discomfort, fear of injection and pain. Also, they lack any sort of control, feedback and safety feature. They have however the advantage of being inexpensive and relatively simple to use. Pump devices on the other hand comprise a large number of elements needed for operation and control, e.g. a processor, electric components, a battery, buttons or switches located on the housing of the device, visual feedback via text or graphic screen, etc. For these reasons, they are expensive, difficult to use and tend to be bulky and uncomfortable. Moreover, they require specialized care, maintenance and cleaning to assure proper functionality and safety for their intended long-term use. Other types of medical devices have been therefore proposed. US2012245515A1 for example, discloses a medical fluid-flow regulating device comprising a medicament reservoir, a pump and a rotor connected to the pump for pumping the medicament from the reservoir when the rotor rotates, the rotor being driven by an external hand-held activation device. An advantage of such a medical fluid-flow regulating device is that it comprises a small number of components and is therefore small and inexpensive. Moreover, it is comfortable, discreet, and easy to use. It is also safe since it further comprises a safe-lock mechanism, which can be unlocked in a specific manner by the hand-held activation device.

EP 2 910 263 A1 discloses a medical fluid-flow regulating device comprising a rotor and a flow-regulator element engaged or engageable with each other via a coupling that, below a torque, allows the flow-regulator element to move upon rotation of the rotor and thereby regulate the fluid flow. This device further comprises a safe-lock mechanism which can be unlocked only when a hand-held device is coupled to it. Even if such a mechanism avoids the operation of the pump and rotor when the hand-held device is not coupled to them, it does not prevent improper use of the device if some problem occurs during the administration of the medicament, such as an obstruction or a partially obstruction along the fluid path. In such cases the device may deliver uncontrolled doses of the medicament without the user being aware of it.

It is therefore further desirable to make medical fluid-flow regulating devices even safer to use by ensuring safe operation in the event something occurs to impede proper functioning of such devices.

This is achieved by the combination of features as described and claimed herein.

SUMMARY OF THE INVENTION

Medical fluid-flow regulating devices are described. Medical fluid-flow regulating devices include a rotor and a flow-regulator element engaged or engageable with each other via a coupling that below a torque and/or fluidic-pressure threshold value allows the flow-regulator element to move upon rotation of the rotor and thereby regulate fluid flow. In particular, medical fluid-flow regulating devices further comprise a blocking unit that above the torque and/or fluidic-pressure threshold value irreversibly blocks the rotor or the flow-regulator element or the coupling between the rotor and the flow-regulator element resulting in irreversible inactivation of the medical fluid-flow regulating device. Systems comprising a medical fluid-flow regulating device and methods of detecting irreversible inactivation of medical fluid-flow regulating devices are also described. In this way, occurrence of any event that impedes proper operation of the medical-fluid flow regulating device such as for example clogging, emptied fluid reservoir, mechanical failure, as long as it causes an increase of the torque and/or fluidic pressure above a threshold value causes irreversible inactivation of the fluid-flow regulating device that prevents any further attempt to use it, regardless of the particular event.

Medical fluid-flow regulating devices according to the invention are characterized by a blocking unit which comprises an irreversible stop element that impedes the rotor from rotating again after the blocking unit becomes effective.

A "medical fluid-flow regulating device" refers to a device which is configured to be placed in contact with a patient and to perform medical treatment by regulating the flow of a fluid in the patient's body or into the patient's body or out of the patient's body. "Regulating the flow" means changing by e.g. increasing, decreasing, starting, interrupting or resuming the flow of a fluid. This may include pumping a fluid either continuously or at intervals, either at constant or variable flow rate.

"In contact" means either in dermal contact with the patient, e.g. removably fixed, e.g. by an adhesive layer, to the skin of the patient, either directly or indirectly, e.g. only via an infusion element, catheter or the like, or more generally in body contact, comprising the inside of the body, such as fixed at least in part to the inside or outside of the body, e.g. implanted inside the body.

An example of fluid is a medicament for treating a medical condition, e.g. insulin to treat a diabetic condition, a pain-treating drug to treat the symptoms of a chronic disease, an anti-coagulation drug to reduce the risk of thrombosis, e.g. after surgery, a hormone to treat or change other medical conditions, etc. The fluid may be otherwise a body fluid or an external fluid passing through a body fluidic conduit.

According to certain embodiments medical fluid-flow regulating devices are medical infusion devices configured to deliver trans-dermally or intravenously multiple doses of a fluidic medicament to a patient without the need of multiple injections. A typical example of a patient is a diabetic patient requiring frequent doses of insulin, e.g. in correspondence to each meal. According to one embodiment, the medical fluid-flow regulating device is an implantable device or a device partly in the body and partly out of the body, e.g. a catheter. The medical fluid-flow regulating device may be embodied as a valve device configured to enable/disable fluid flow or vary the flow rate of a fluid, e.g. a body fluid, or as a continuous infusion device, configured to deliver a continuous flow of a medicament with a flow rate, which may be changed over time.

A "rotor" refers to a rotatable medical fluid-flow regulating device component, which allows the medical fluid-flow regulating device to regulate the flow of a fluid upon rotation, and in particular upon application of a force or torque. The term "rotation" is used here generically to indicate any number of revolutions or fractions of a revolution without reference to time. Also, rotation may occur in opposite or alternate directions, with constant motion, accelerated motion, or pulse, oscillatory motion or combinations thereof.

A "flow-regulator element" refers to a component of a flow regulator configured to regulate the flow of a fluid, typically through a fluidic conduit, e.g. the flow of a fluid medicament through an infusion element.

The rotor and the flow-regulator element are engaged or engageable with each other directly or indirectly via a coupling. The rotor and the flow-regulator element may be arranged in a pre-operational position, in which they are not engaged and upon rearrangement into an operation position become engaged.

A "coupling" refers to a mechanism linking the rotor and the flow-regulator element in a manner that force can be transferred between the rotor and the flow-regulator element, including from the rotor to the flow-regulator element and/or vice versa, and by which movement of any one of the rotor, the flow-regulator element, the coupling results in the movement of at least one of the other two. The coupling may be an element or group of elements separate from the rotor and the flow regulator-element. However, the coupling also may be an integral part of the rotor and/or of the flow-regulator element. According to certain embodiments the coupling is a mechanical coupling. According to other embodiments the coupling is a gear coupling. The coupling may be however of other types, e.g. inductive, e.g. a magnetic or electromagnetic coupling.

Movement may include rotation, translation, oscillation or combinations thereof in any direction or in alternate directions.

In particular, when the rotor and the flow-regulator-element are engaged via the coupling, the flow-regulator element may move upon rotation of the rotor and thereby regulate fluid flow as long as the torque is below a threshold value and/or the fluidic-pressure is below a threshold value.

According to certain embodiments, the flow-regulator element is an axial pump element that upon translation either directly or indirectly causes displacement of fluid. In certain embodiments, the axial pump element is a push or pull element like a plunger or piston or is coupled to a plunger or piston that is coupled or couplable to a syringe-like or cartridge-like fluid reservoir. According to this embodiment, rotation of the rotor causes translation of the flow-regulator element via the coupling that in turn causes displacement of fluid.

According to other embodiments the flow-regulator element can be either an element of a pump or of a valve for regulating the flow of a fluid.

A "pump" may be any sort of pumping mechanism, e.g. a peristaltic pump, a membrane pump, a micropump, as known in the art, and configured for pumping a fluid through a fluidic conduit. A "valve" may be any sort of valve having at least one valve inlet and at least one valve outlet for interrupting, resuming, diverting, decreasing or increasing the flow of a fluid in a fluidic conduit.

The term "fluidic conduit" is used herein to indicate any sort of structure for transporting fluid and/or storing and/or receiving fluid. It may be made of metal or polymer or composite material, made of one piece or more pieces directly or indirectly connected to each other. The fluidic conduit is not limited to any particular geometry or form and may comprise parts having different cross-sections, such as e.g. a part with a tubular or substantially cylindrical cross-section and a part with a substantially rectangular cross-section. In particular, the fluidic conduit may be embodied as a tubing, a fluidic vessel or channel, and may comprise a chamber, a reservoir, an infusion element, etc.

The term "fluid" indicates a medium or a substance in a medium, typically a liquid, capable of flowing through the fluidic conduit and whose flow regulation results in medical treatment. An example of fluid is a medicament for treating a medical condition, e.g. insulin to treat a diabetic condition, a pain-treating drug to treat the symptoms of a chronic disease, an anti-coagulation drug to reduce the risk of thrombosis, e.g. after surgery, a hormone to treat or change other medical conditions, etc. The fluid also may be a body fluid or an external fluid passing through a body fluidic conduit.

Medical fluid-flow regulating devices further include a blocking unit. A "blocking unit" refers to a safety feature that at the occurrence of an event that impedes proper operation of the medical fluid-flow regulating device irreversibly blocks operation of the medical fluid-flow regulating device, therefore preventing use or further use. For example, medical fluid-flow regulating devices may experience clogging, for example because of the formation of precipitates, crystals or particle aggregates in a fluidic conduit or at the exit of the fluidic conduit, in particular of the infusion element. Also, mechanical failures may occur, e.g. due to manufacturing defects or to mishandling of the medical fluid-flow regulating device. For example, some of the parts may be defective, e.g. broken, deformed or out of position, possibly due to mishandling or impact, e.g. a fall. Also, in case the medical fluid-flow regulating device comprises an internal fluid reservoir, it should be taken into account that the fluid can finish at some point and when the reservoir is emptied the medical fluid-flow regulating device can no longer operate properly. It is therefore important for safety reasons that, whenever an event that impedes proper functioning occurs, the medical fluid-flow regulating device is no longer used rather than attempting to repair it or solve the problem. The blocking unit therefore has the function of irreversibly inactivating the medical fluid-flow regulating device in the occurrence of such an event so that it can no longer be used, i.e. it is permanently inactivated. In particular, medical fluid-flow regulating devices are so designed that in the occurrence of such an event, the torque or the force required for rotating the rotor and moving the flow-regulator element, and/or the fluidic pressure, depending on the event, increases. Also, medical fluid-flow regulating devices are designed so that as long as the torque and/or the fluidic pressure remain below a torque or fluidic-pressure threshold value the blocking unit remains disengaged from any of the rotor, the fluid-flow regulator element or the coupling thereby allowing the flow-regulator element to move upon rotation of the rotor and thereby regulate fluid flow. Whereas as soon as the torque and/or the fluidic pressure increase above the threshold value as a result of any of the above events, any one or more of the rotor, the flow-regulator element, the coupling, the blocking unit or any elements thereof are displaceable with respect to each other resulting in irreversible engagement with the blocking unit and therefore in permanent inactivation of the medical fluid-flow regulating device.

According to certain embodiments, the rotor is displaceable with respect to the blocking unit above the torque and/or fluidic-pressure threshold value thereby irreversibly engaging with the rotor-blocking unit and preventing the rotor to be rotated.

According to certain embodiments, the blocking unit or any element thereof is displaceable with respect to the rotor above the torque and/or fluidic-pressure threshold value thereby irreversibly engaging with the rotor and preventing the rotor from rotating.

According to certain embodiments, the blocking unit comprises a membrane that above the fluidic-pressure threshold value is expanded such as to directly or indirectly block the rotor and prevent the rotor to be rotated.

According to certain embodiments, the flow-regulator element or the coupling between the rotor and the flow-regulator element is displaceable with respect to the rotor or is deformable above the torque or fluidic-pressure threshold value thereby functioning as a blocking unit for the rotor or is adapted to move the blocking unit into engagement with the rotor.

The medical fluid-flow regulating device may comprise a reservoir. The reservoir may be any type of container with any shape, suitable for containing a fluid of choice, in particular a medicament. The reservoir, thus preferably comprises a chemical- and/or bio-compatible material inert to the fluid to be contained. According to certain embodiments the reservoir is pre-loaded with the fluid in the manufacturing process. The reservoir may thus be suitable for storing a fluid within the device for a long period of time, e.g. several months or years before the device is used. According to certain embodiments the reservoir is configured to be loaded with the fluid by the user, i.e. the patient or care giver, before use. According to certain embodiments the reservoir is configured to be loaded into or onto the device before use, either before or after loading the reservoir with the fluid.

According to certain embodiments the reservoir is a collapsible pouch, configured to expand from a collapsed status to an expanded status upon loading the reservoir with the fluid and from an expanded status to a collapsed status upon emptying the reservoir, e.g. upon pumping the fluid.

According to certain embodiments the reservoir is a syringe-like, carpule-like or cartridge-like reservoir. It may be made, at least in part of glass, plastics, rubber or combinations thereof.

The medical fluid-flow regulating device may comprise an infusion element. The infusion element may be configured for the trans-dermal infusion of the fluid, i.e. configured to remain in a trans-dermal position for the duration of use of the medical fluid-flow regulating device such as to allow infusion of a dose of medicament from the medical fluid-flow regulating device into the body when requested. The infusion element may comprise a thin needle insertable at a controlled depth, a cannula, a catheter, or other form of hollow fluid transport conduit, insertable e.g. via a removable needle, and configured to infuse a medicament. The infusion element may comprise or be made of metal such as steel, of a ceramic material, of a silica-based material, of a polymeric material such silicone or Teflon, or any composite thereof. The infusion element may comprise one or more outlets, e.g. a plurality of micro-needles, configured to penetrate the skin and/or infuse the medicament in parallel or sequentially. The infusion element may comprise a triggering element, comprising e.g. a resilient element, e.g. a spring, configured to trigger skin penetration.

Systems comprising above-described medical fluid-flow regulating devices are also provided. Whereas the medical fluid-flow regulating device may be disposable or semi-disposable, the system further comprises a hand-held activation device, separate from the medical fluid-flow regulating device, that is reusable. In particular, the activation device comprises a drive unit for magnetically or inductively rotating the rotor of the medical fluid-flow regulating device and a sensor for detecting rotation of the rotor.

The drive unit may function also as an unlocking unit for the rotor. In particular, medical fluid-flow regulating devices may comprise an additional safety lock mechanism that temporarily locks the rotor and prevents it from rotating in the absence of the hand-held activation device. The rotor may be unlocked and rotated by temporarily docking the activation device to the medical fluid-flow regulating device in an energy transfer position, which enables the unlocking/drive unit to inductively or magnetically transfer an energy required to unlock the safe-lock mechanism and for rotating the unlocked rotor. The rotor is again lockable by removing the activation device from the energy-transfer position, thus removing the source of energy that maintains the rotor unlocked.

According to certain embodiments, the safe-lock mechanism and the blocking unit may comprise shared components.

According to certain embodiments, the rotor comprises a central body and a margin extending from the central body. The margin includes at least one actionable section that is movable from a rest position to a stretched position with respect to the central body upon application of a force by the drive unit and is configured to resiliently return to the rest position upon removal of the force, where in the rest position the rotor is locked by the safe-lock mechanism and is unable to rotate and in the stretched position the rotor is unlocked and able to rotate.

However, if the rotor becomes irreversibly blocked by the blocking unit above the torque and/or fluidic pressure threshold value, it cannot be unlocked by the unlocking/drive unit, as this will unlock only the safe-lock mechanism and not the blocking unit. The medical fluid-flow regulating device can therefore no longer be used.

The sensor for detecting rotation of the rotor typically comprises at least a first sensor component in the medical fluid-flow regulating device, which is adapted to be detected by at least a second sensor component in the hand-held activation device.

In general, the term "in the medical device" or "in the hand-held device" as used herein indicates that the object referred to is part of or belongs to, e.g. specifically associated with, the medical device or the hand-held device respectively, either inside or outside, e.g. on the housing, or otherwise coupled to.

According to one embodiment, the sensor is a proximity sensor, able to detect the presence and preferably the distance of a proximity target without physical contact.

For example, the first sensor component may comprise at least one metal proximity target and the second sensor component may be an inductive sensor, which is adapted to detect the at least one metal target, by measuring the variation of current in a coil.

Other types of proximity sensors may however be also employed. For example, the second sensor component may be a capacitive or photoelectric sensor, adapted to detect another type of proximity target, e.g. a materially distinguishable component or an electric resistance, by emitting a beam of electromagnetic radiation (infrared, for instance), and measuring changes in the field or return signal.

According to one embodiment the first sensor component comprises at least one magnet or an electromagnet and the second sensor component is a Hall effect sensor, i.e. a transducer that varies its output voltage in response to the magnetic field of the first sensor component. The magnetic field may be induced by a current in a coil or by a permanent magnet.

In general, the at least one first sensor component may comprise at least one element chosen from the group of at least one magnetic element, at least one ferromagnetic element, at least one coil, at least one electromagnetic resonator, at least one photoelectric cell, color changing element, at least one sound transducer or reflector, adapted to be detected by the at least one second sensor component and/or for receiving energy from the drive unit needed for being detected by the at least one second sensor component, e.g. for emitting or reflecting a signal.

In general, the at least one second sensor component comprises at least one element chosen from the group of a force meter, at least one electromagnet, at least one permanent magnet, at least one coil, at least one electromagnetic resonator, at least one sound emitter, at least one sound detector, at least one light emitting element, at least one light detector, for detecting the at least one first sensor component.

The system may comprise a plurality of sensors of the same or different type, e.g. a combination of position sensors.

According to certain embodiments, the system further comprises a controller. A "controller" is a computing unit, embodied e.g. as a programmable logic controller running a computer-readable program provided with instructions to perform operations in accordance with one or more process operation plans. The controller is programmed to control if rotation of the rotor fails despite operation of the drive unit for rotating the rotor and/or if operation of the drive unit corresponds to intended rotation of the rotor, based on feedback signals provided by the sensor.

The controller may be further programmed to control the drive unit or the unlocking/drive unit.

According to one embodiment the controller is programmed to interpret detection of failure of rotation of the rotor as an increase of the torque and/or of the fluidic pressure above the threshold value and to associate it to a condition of irreversible inactivation of the fluid-flow regulating device.

According to one embodiment the controller is programmed to warn and/or to stop or prevent operation of the drive unit and/or prevent further use of the fluid-flow regulating device if detection of rotation of the rotor fails.

Methods that prevent use of medical fluid-flow regulating devices are also provided. In particular, a method of detecting irreversible inactivation of the medical fluid-flow regulating device is described. The method comprises detecting if the rotor fails to rotate despite operation of the drive unit for rotating the rotor.

According to certain embodiments, the methods further comprise warning and/or stopping or preventing operation of the drive unit and/or preventing further use of the fluid-flow regulating device if detection of rotation of the rotor fails.

The warning may include an indication to replace the medical fluid-flow regulating device.

The warning also may include information about the type of event, e.g. clogging or emptied reservoir.

The present invention is further described in the detailed description below with reference to the following drawings schematically representing exemplary embodiments.

BRIEF DESCRIPTION OF THE FIGURES

FIG. 1b is an exploded view of the same inner components of the medical fluid-flow regulating device as shown in FIG. 1a.

FIG. 2a is a top partial view of a second embodiment of medical fluid-flow regulating device showing only some of the inner components for clarity purpose.

FIG. 2b is an exploded view of the same inner components of the medical fluid-flow regulating device as shown in FIG. 2a.

FIG. 2c is a perspective bottom view of the same inner components of the medical fluid-flow regulating device of FIGS. 2a and 2b in assembled form.

FIG. 3b is a perspective top view of the same inner components of the medical fluid-flow regulating device of FIG. 3a.

FIG. 4 shows schematically a system comprising a medical fluid-flow regulating device and a hand-held activation device as well as a method of detecting irreversible inactivation of the medical fluid-flow regulating device.

DETAILED DESCRIPTION

Figure 1A:
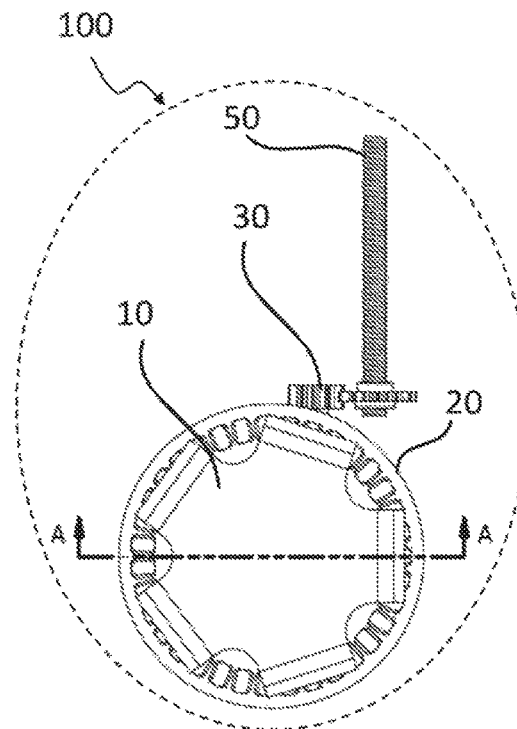
FIG. 1a is a top partial view of a first embodiment of medical fluid-flow regulating device showing only some of the inner components for clarity purpose.
Figure 1B:
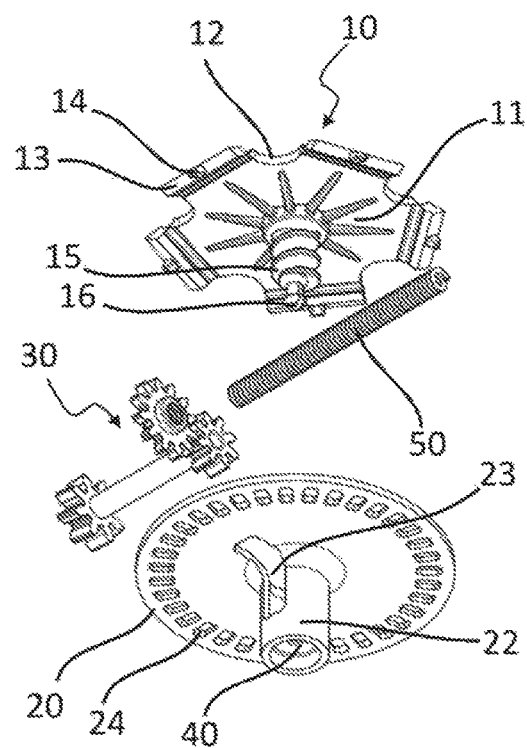
Figure 1C:
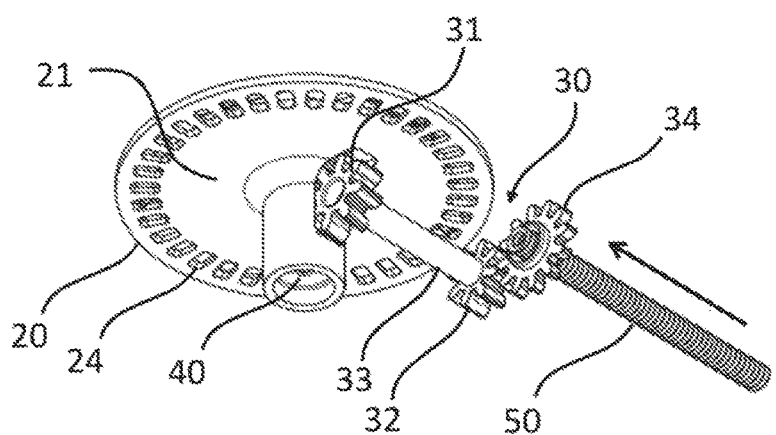
FIG. 1c is a perspective bottom view of the same inner components of the medical fluid-flow regulating device of FIGS. 1a and 1b in assembled form.

With combined reference to FIG. 1a, FIG. 1b and FIG. 1c, a first embodiment of a medical fluid-flow regulating device 100 is described. In particular, only some of the inner components relevant to the present disclosure are illustrated, as a top view, exploded view and perspective bottom view in FIG. 1a, FIG. 1b and FIG. 1c respectively. The medical fluid-flow regulating device 100 comprises a rotor 10 and a flow-regulator element 50 engaged with each other via a coupling 30. The medical fluid-flow regulating device 100 further comprises a safe-lock mechanism 20 and a blocking unit 40.

The rotor 10 comprises a central body 11 and a margin 12 extending from the central body 11. The margin comprises a plurality of actionable sections 13 comprising a respective number of protrusions 14. The rotor as well as the other elements of the present device are herein described only with reference to the essential parts that are relevant to the present invention, to avoid unnecessary lengthening of the specification. It should in fact be understood that the general structure and functioning of medical fluid-flow regulatory devices is known from the prior art, in particular from the previous patent applications of the same Applicants, namely EP 2 379 132, EP 2 617 445, EP 2 674 177, EP 2 764 881 and EP 2 910 263. For example, more details about this kind of rotor 10 are described in EP2910263A1.

The rotor 10 further comprises a shaft 15 comprising a spiral groove in the form of a screw thread. At the end of the shaft 15 the rotor comprises an irreversible stop element, i.e. a snap-fit fastener 16.

The flow-regulator element 50 may have a shape of a helical spring with consecutive turns contacting each other in a relaxed condition. The turns thus form a screw-like thread that can be coupled to a gear wheel 34. The spring 50 is rigid in the axial longitudinal direction due to the fact that the turns contact each other so that it can be used as an axial pump element with a push function. However, the spring 50 is also flexible in a non-axial direction and can therefore be bent in order to minimize space needs while retaining its rigidity in the axial longitudinal direction.

The coupling 30 is a gear coupling comprising a first gear wheel 31, a second gear wheel 32, a rigid connector 33 connecting the first gear wheel 31 to the second gear wheel 32 so that the second gear wheel 32 is rotatable together with the first gear wheel 31, and the third gear wheel 34. In particular, the first gear wheel 31 has a pitch that matched the thread of the shaft 15 of the rotor 10 and is coupled to the shaft 15 in a manner that when the rotor 10 rotates the first gear wheel 31 and therefore also the second gear wheel 32 rotate. The second gear wheel 32 is in turn coupled to the third gear wheel 34 via an external gear and the third gear wheel 34 is coupled to the spring 50 via an inner gear. The third gear wheel 34 is screwed about the spring 50 like a nut. Upon rotation of the rotor 10 thus also the third gear wheel 34 is rotatable. The flow-regulator element 50 is prevented from rotating by a sort of guide not shown in the figures. Hence, upon rotation of the third gear wheel 34 the spring 50 can move in the axial direction. In other words, at each rotation of the rotor 10 the spring 50 can be advanced in the axial direction. The coupling 30 may include a different number and shape of components than the ones shown in this example. For example, the wheel 34 may be coupled directly to the shaft 15. The spring 50 can be directly or indirectly coupled to a syringe-like reservoir (not shown) comprising a fluid so that advancement of the spring 10 results in ejection of fluid from the reservoir.

The safe-lock-mechanism 20 comprises a round plate 21 having a diameter similar to that of the rotor 10 and arranged parallel to the central body 11 of the rotor 10. The plate 21 comprises a plurality of holes 24 arranged at regular intervals about its circumference. The safe-lock mechanism 20 further comprises a central hollow body 22 into which the shaft 15 of the rotor 10 loosely fits. The hollow body 22 further comprises a window 23 that allows coupling of the shaft 15 with the first gear wheel 31. The safe-lock mechanism 20 is fixed with respect to the medical fluid-flow regulating device 100 and remains stationary when the rotor 10 is allowed to rotate.

The blocking unit 40 is in this embodiment part of the safe-lock mechanism 20. In particular, it is embodied as a recess at the bottom of the hollow body 22 comprising an upper concave part ending with a narrower aperture at the bottom for receiving in an irreversible manner the snap-fit fastener 16 of the rotor 10. The blocking unit 40 could be however completely separated and is in any case independent in its function from the function of the safe-lock mechanism 20 whereas together they provide an increased standard of security to the medical fluid-flow-regulating device 100.

The manner of operating the medical fluid-flow-regulating device 100 and the relationship between the different parts described above will be now described with reference to FIG. 1d, FIG. 1e and FIG. 1f.

Figure 1D:
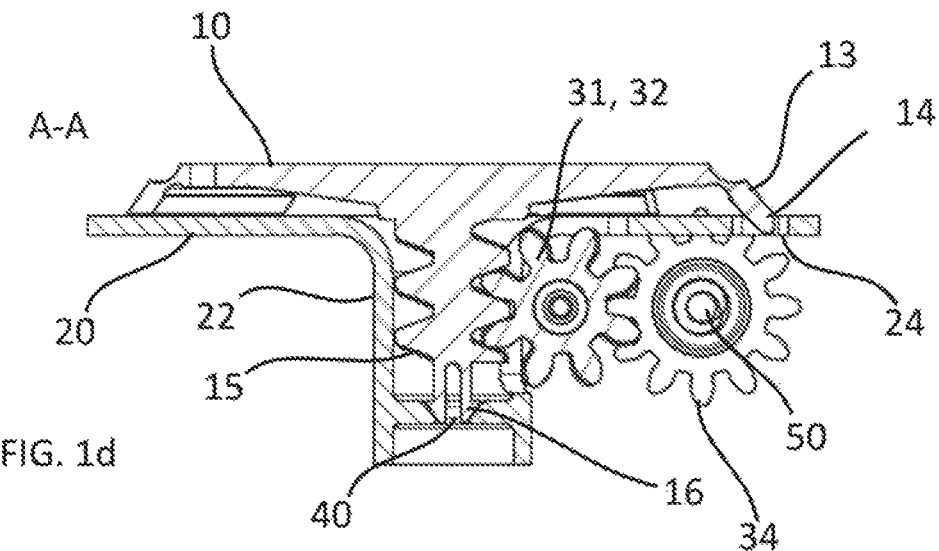
FIG. 1d is a cross-sectional view of the same inner components of the medical fluid-flow regulating device as shown in FIG. 1a though line A-A of FIG. 1a, in a standby condition.

FIG. 1d is a cross-sectional view of the same inner components of the medical fluid-flow regulating device 100 as shown in FIG. 1a though line A-A of FIG. 1a, in a standby condition, in which the rotor 10 is locked by the safe-lock mechanism 20 and unable to rotate. In particular, when fluid flow regulation is not needed, the actionable sections 13 of the rotor 10 are in a rest position and the protrusions 34 fit into any of the holes 24 of the plate 21 of the safe-lock mechanism 20 that they find themselves in correspondence to, thereby locking the rotor 10 and preventing that the rotor 10 is accidentally rotated when not needed. The snap-fit fastener 16 is out of engagement with the blocking unit 40. In particular, the snap-fit fastener 16 comprises two halves, each having a leg attached to the end of the shaft 15 and a semi-conical tip attached to the leg, larger at the side of the leg and narrower at the extremity, and with a gap between the two halves, such as to form two hook-shaped snap-fit clips biasable towards each other upon application of a sufficient force and capable of resiliently returning to their original position in absence of the force. In the stand-by position of FIG. 1*d* the outer geometry of the tip of the snap-fit fastener 16 is complementary and fits into the upper concave part of the blocking unit 40, which forms a base on which the rotor 10 can sit and that contributes to maintain the shaft 15 aligned to the hollow body 22 and to minimize any tilt upon rotation.

Figure 1E:
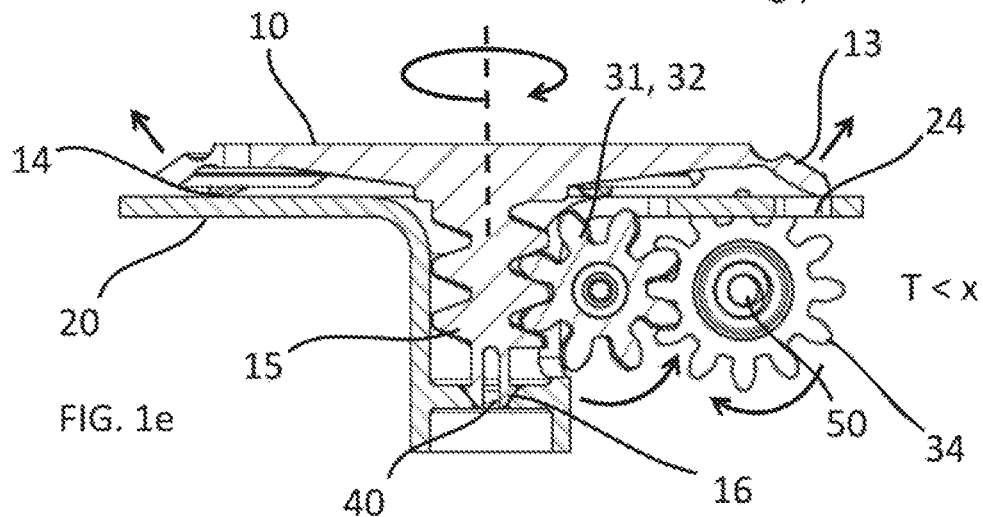
FIG. 1e is across-sectional view similar to that of FIG. 1d, with the components in an operational condition.

FIG. 1*e* is a cross-sectional view similar to that of FIG. 1*d* and showing the same components in an operational condition. In particular, the actionable sections 13 comprise ferromagnetic elements that upon application of a magnetic force provided by an external hand-held activation device (shown in FIG. 4) cause the actionable sections 13 to stretch as indicated by arrows in the figure and the protrusions 14 to get out of the holes 24 of the safe-lock mechanism 20. The rotor 10 is thereby unlocked and capable of being rotated by application of another magnetic force by the same hand-held activation device. For more details about the operation of such a type of rotor reference is made to the disclosure in EP2910263A1.

In particular, when the rotor 10 is unlocked and the torque T is below a threshold value x (T<x) rotation of the rotor 10 results in translation of the flow-regulator element 50 thereby regulating fluid flow. The snap-fit fastener 16 as long as the torque T remains below the threshold value x (T<x) remains out of engagement with the blocking unit 40.

After flow regulation, e.g. after infusion of a dose of medicament, by rotating the rotor 10 as necessary, the actionable sections 13 are configured to resiliently return to the original rest position upon removal of the hand-held activation device and thereby of the magnetic force, thereby engaging again with the safe-lock mechanism 20 and locking the rotor 10, as illustrated in FIG. 1*d*.

Figure 1F:
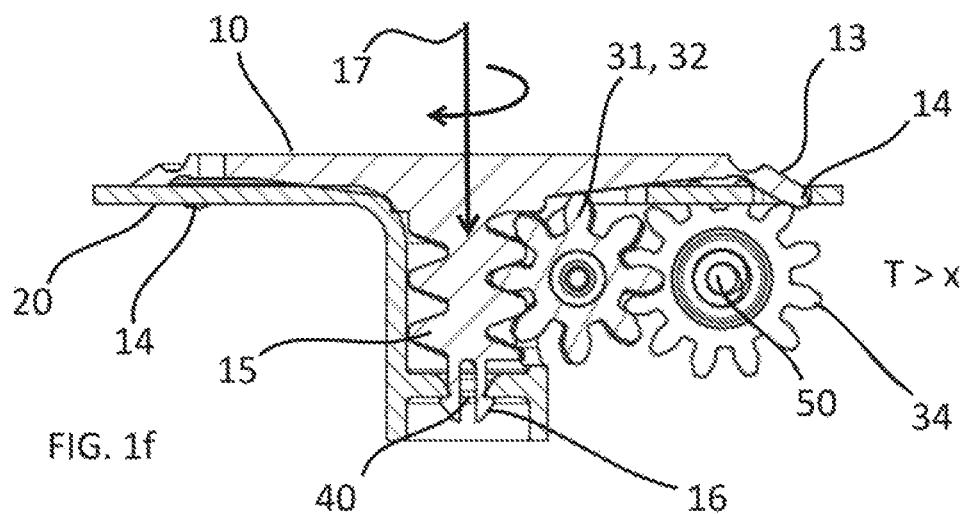
FIG. 1f is across-sectional view similar to that of FIG. 1d, with the components in an irreversibly inactivated condition.

FIG. 1*f* is a cross-sectional view similar to that of FIG. 1*d*, showing the components in an irreversibly inactivated condition. In particular, when the torque T is above a threshold value x (T>x), the rotor 10, although unlocked and although energy is being provided to it by the external hand-held activation device for rotating, is unable to cause movement of the flow-regulator element 50. This may occur for example in case of clogging, in which case the flow-regulator element 50 can no longer advance due to an increase of the fluidic pressure. Analogously, when the syringe-like reservoir (not shown) is empty the flow-regulator element 50 can no longer advance, having reached a mechanical stop. When energy is provided to the rotor 10 by the hand-held activation device an increased torque is therefore experienced. When trying to rotate the rotor 10, due to the fact that the flow-regulator element 50 cannot move in the axial direction and therefore the gear wheels 31, 32, 34 cannot rotate, it is the rotor 10 that tends to move in the axial direction along its axis of rotation 17 as indicated by the arrow in FIG. 1*f*. If the force is sufficient for the snap-fit fastener 16 to deform and to pass through the aperture of the blocking unit 40, the rotor 10 is screwed downwards and the snap-fit fastener 16 becomes engaged with the blocking unit 40 in an irreversible manner as shown in FIG. 1*f*. The torque threshold value is therefore related to the force required for the snap-fit fastener 16 to become engaged with the blocking unit 40. If the force required for the rotor 10 to rotate and to move the flow-regulator element 50 is larger than the force required for the snap-fit fastener 16 to become engaged with the blocking unit 40, the rotor 10 is pushed in the axial direction and becomes permanently engaged with the blocking unit 40. By doing so, the actionable sections 13 and the protrusions 14 become engaged with the safe-lock mechanism 20 in a manner that can no longer be unlocked. The rotor 10 is therefore irreversibly inactivated and prevented to further rotate. This is an example of how the rotor 10 is displaceable with respect to the blocking unit 40 above the torque and/or fluidic-pressure threshold value thereby irreversibly engaging with the rotor-blocking unit 40 and preventing the rotor 10 to be rotated.

Figure 5A:
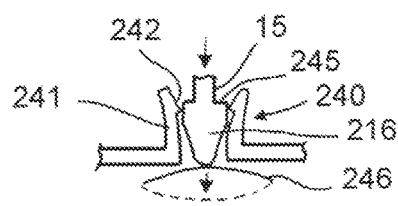
FIGS. 5a and 5b are cross-sectional views of a particular of the irreversible blocking unit according to variants of the embodiments shown in FIGS. 1d-1f.
Figure 5B:
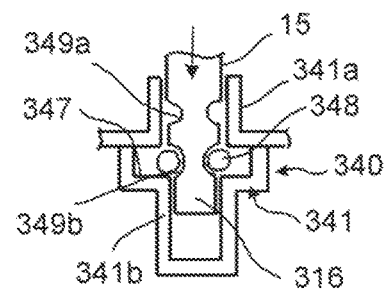

FIGS. 5*a* and 5*b* show variants of the snap-fit engagement of the snap-fit fastener with rotor-blocking unit.

With reference to FIG. 5*a*, the rotor-blocking unit 240 comprises a seat 241 having an upper rim 242 with a hooked profile. The seat 241 has an open bottom, underneath of which a bi-stable membrane 246 is positioned. The membrane 246 can have an upper position and a lower position (dotted line in the figure). In normal operational conditions, the bottom end of the rotor 10 rests on this membrane.

The shaft 15 of the rotor 10 ends with a snap-fit fastener 216 comprising an upwardly-facing shoulder 245.

When the rotor 10 is forced to move downward (see the arrow in FIG. 5*b*) as explained above, i.e. when the flow-regulator element 50 is prevented from advancing, the snap-fit fastener 216 moves downwards and pushes the bi-stable membrane 246 in its lower position. At the same time, the shoulder 245 engages the hooked profile of the upper rim 242, so that an irreversible engagement is achieved. With reference to FIG. 5*b*, the rotor-blocking unit 340 comprises a seat 341 comprising an upper guiding sleeve 341*a* and a lower recess 341*b*. The lower recess 341*b* comprises an upwardly-facing internal shoulder 347 hosting a supporting an elastic ring 348.

The shaft 15 of the rotor 10 ends with a snap-fit fastener 316 comprising at least one longitudinally-spaced groove 349*a*, 349*b*, sized in order to snap-fit with the elastic ring 348. In normal operational conditions, the elastic ring 348 engages the lower groove 349*b*.

When the rotor 10 is forced to move downward (see the arrow in FIG. 5*c*) as explained above, i.e. when the flow-regulator element 50 is prevented to advance, the snap-fit fastener 316 moves downwards. Upon a proper torque, the elastic ring 349 dilates, allowing such a downward movement of the snap-fit fastener 316. Therefore, when the rotor 10 end abuts against the bottom the recess 341*b*, the elastic ring 348 engages the upper groove 349*a*, which irreversibly locks the rotor 10 in its lower, non-operational condition.

With combined reference to FIG. 2*a*, FIG. 2*b* and FIG. 2*c*, a second embodiment of medical fluid-flow regulating device 100' is described. The medical fluid-flow regulating device 100' of FIG. 2*a*-2*c* is similar to the medical fluid-flow regulating device 100 of FIG. 1*a*-1*c*, where like features are given like reference numbers.

In particular, the medical fluid-flow regulating device 100' comprises a rotor 10' and a flow-regulator element 50 engaged with each other via a coupling 30'. The medical fluid-flow regulating device 100' further comprises a safe-lock mechanism 20' and a blocking unit 40'.

The main difference between the rotor 10' and the rotor 10 of FIG. 1*a*-1*c* is the absence of a snap-fit fastener at the end of the shaft 15 and the presence of thicker relief structures 18 on the bottom side of the central body 11 arranged radially outwards from the shaft 15 towards the margin 12.

The flow regulator element 50 is the same as that of the embodiment of FIG. 1a-1c. The coupling 30' is similar to that of the embodiment of FIG. 1a-1c with the difference that the coupling 30' further comprises a protruding bar 35 embodied as an extension of the connector 33, however on the external side of the gear wheel 31.

The safe-lock mechanism 20' is similar to that of the embodiment of FIG. 1a-1c. In particular, it comprises the same plate 21 and a central hollow body 22' into which the shaft 15 of the rotor 10' loosely fits. The hollow body 22' further comprises a window 23 that allows coupling of the shaft 15 with the first gear wheel 31. The safe-lock mechanism 20' is fixed with respect to the medical fluid-flow regulating device 100' and remains stationary when the rotor 10' is allowed to rotate.

However, the blocking unit 40' is different from that of the embodiment of FIG. 1a-1c. In particular, the blocking unit 40' is still part of the safe-lock mechanism 20' but is arranged at a different position with respect to the previous embodiment and is based on a different working principle. More in particular, the blocking unit 40' comprises a lever arranged through the plate 21 of the safe-lock mechanism 20', at a position that faces and nearly touches the protruding bar 35 of the coupling 30'.

Figure 6:
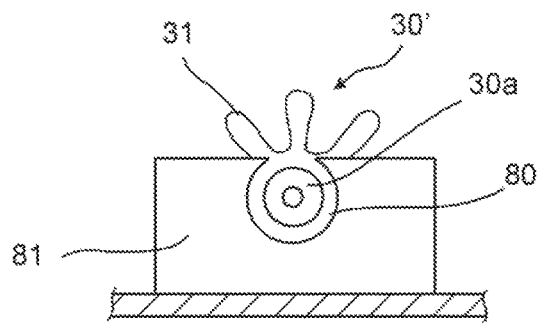
FIG. 6 is a cross-sectional view of a particular of the irreversible blocking unit in the embodiment shown in FIGS. 2d-2f.

As also shown in FIG. 6, the coupling 30' has an end proximal to the flow-regulator device 50 and a distal end 30a corresponding to the end of the protruding bar 35. The distal end 30a is hinged in a seat 80 located on a supporting element 81 that protrudes from the internal wall of the housing of the device. The supporting element 81 is made of a flexible material. The seat 80 has a semi-circular shape, whose open section is smaller than the diameter of the distal end 30a of the coupling 30'. Since the supporting element 81 is flexible, the distal end 30a of the coupling 30' can be displaced from its seat 80 upon the application of a certain upward force.

The way of operating of the medical fluid-flow-regulating device 100' and in particular of the blocking unit 40' will be now described with reference to FIG. 2d, FIG. 2e and FIG. 2f.

Figure 2D:
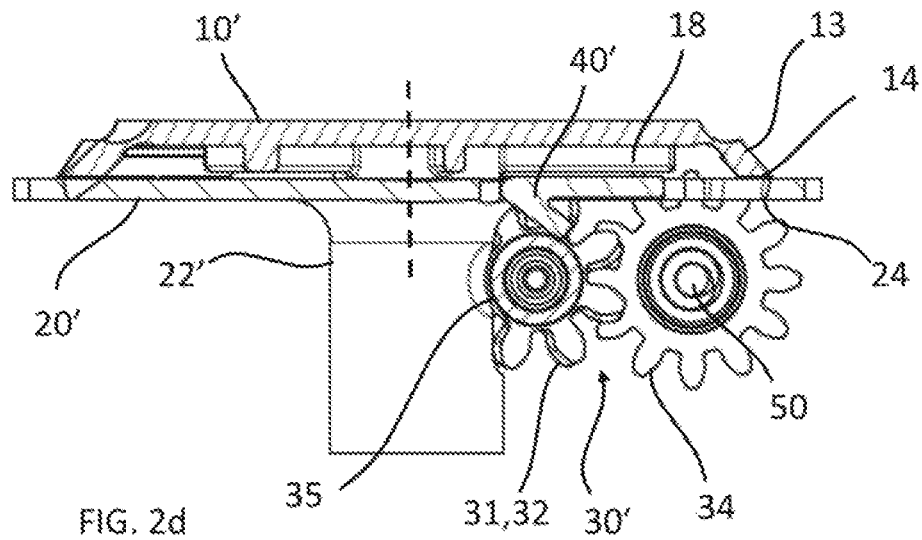
FIG. 2d is a cross-sectional view of the same inner components of the medical fluid-flow regulating device as shown in FIG. 2a though line A-A of FIG. 2a, in a standby condition.

FIG. 2d is a cross-sectional view of the same inner components of the medical fluid-flow regulating device 100' as shown in FIG. 2a through line A-A of FIG. 2a, in a standby condition, in which the rotor 10' is locked by the safe-lock mechanism 20' and unable to rotate. In particular, analogously to the embodiment of FIG. 1d, when fluid flow regulation is not needed, the actionable sections 13 of the rotor 10' are in a rest position and the protrusions 34 fit into any of the holes 24 of the plate 21 of the safe-lock mechanism 20' that they find themselves in correspondence to, thereby locking the rotor 10' and preventing that the rotor 10' is accidentally rotated when not needed. The lever of the blocking unit 40' is parallel to the plane of the plate 21 of the safe-lock mechanism 20' and does not impede in this position rotation of the rotor 10' if unlocked.

Figure 2E:
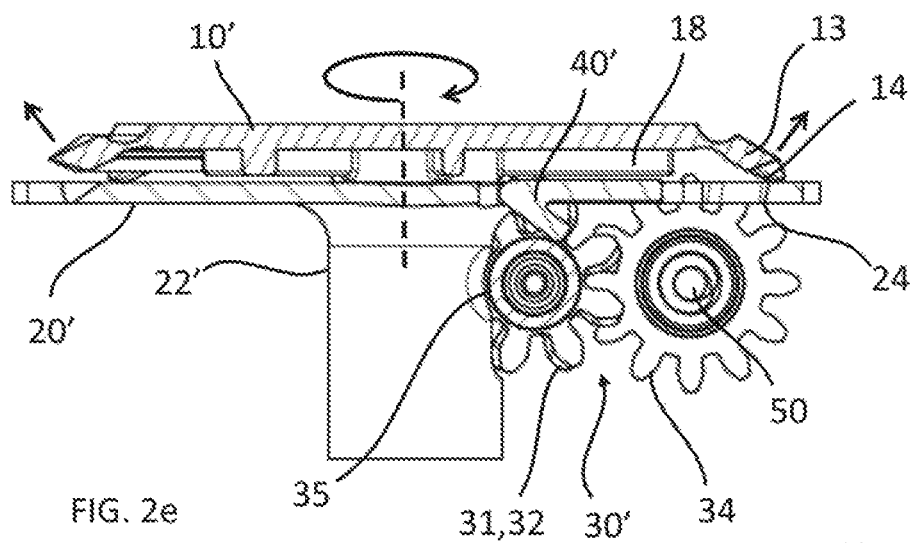
FIG. 2e is across-sectional view similar to that of FIG. 2d, with the components in an operational condition.

FIG. 2e is a cross-sectional view similar to that of FIG. 2d and showing the same components in an operational condition. In particular, upon application of a magnetic force provided by an external hand-held activation device (shown in FIG. 4) the actionable sections 13 are stretched as indicated by the arrows in the figure and the protrusions 14 get out of the holes 24 of the safe-lock mechanism 20', analogously to the embodiment of FIG. 1e. The rotor 10' is thereby unlocked and capable of being rotated by application of another magnetic force by the same hand-held activation device.

In particular, when the rotor 10' is unlocked and the torque T is below a threshold value x (T<x) rotation of the rotor 10' results in translation of the flow-regulator element 50 thereby regulating fluid flow. The lever of the blocking unit 40' as long as the torque T remains below the threshold value x (T<x) remains parallel to the plane of the plate 21 of the safe-lock mechanism 20' and in this position does not impede rotation of the rotor 10'.

After flow regulation, e.g. after infusion of a dose of medicament, by rotating the rotor 10' as necessary, the actionable sections 13 are configured to resiliently return to the original rest position upon removal of the hand-held activation device and thereby of the magnetic force, thereby engaging again with the safe-lock mechanism 20' and locking the rotor 10', as illustrated in FIG. 2d.

Figure 2F:
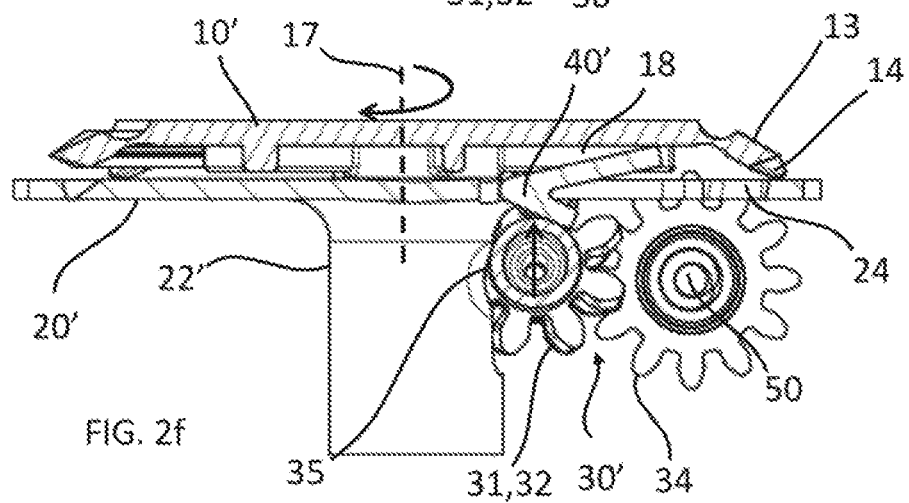
FIG. 2f is across-sectional view similar to that of FIG. 2d, with the components in an irreversibly inactivated condition.

FIG. 2f is a cross-sectional view similar to that of FIG. 2d and showing the same components in an irreversibly inactivated condition. In particular, when the torque T is above a threshold value x (T>x) for any of the reasons mentioned above, e.g. due to the fact that the flow-regulator element 50 cannot move in the axial direction, when trying to rotate the rotor 10', it is the rotor 10' that tends to move in the axial direction along its axis of rotation 17. However, unlike in the embodiment of FIG. 1f, the rotor 10' cannot move in the axial direction either, as there is no room for it to move axially with respect to the safe-lock mechanism 20'. In this case, it is part of the coupling 30' and in particular the part comprising the gear wheels 31, 32, the connector 33 and the protruding bar 35 that, when trying to rotate the rotor 10', is moved upwards towards the plate 21 of the safe-lock mechanism 20'. The distal end 30a of the coupling 30' is displaced from its seat 80. Due to the particular shape of the seat 80, as explained above, even if the upward force is removed, the distal end 30a of the coupling 30' cannot enter again in the seat 80, but it can only rest above it. The seat 80 therefore forms the irreversible stop element according to the invention meaning.

Due to the upward displacement of the coupling 30', the protruding bar 35 pushes the lever of the blocking unit 40', which is irreversibly pivoted out of the plate 21 against the lower surface of the central body 11 of the rotor 10'. Due to the presence of the relief structures 18, even if the rotor is unlocked and additional force was provided, the rotor 10' is unable to rotate due to the presence of the lever of the blocking unit 40' hitting against a relief structure 18 and blocking the rotor 10'. The torque threshold value is in this case related to the force required to displace the coupling 30' and for the lever of the blocking unit 40' to pivot out of the plate 21. If the force required for the rotor 10' to rotate and to move the flow-regulator element 50 is larger than the force required for the coupling 30' to be displaced and to pivot the lever of the blocking unit 40', then the rotor 10' is permanently blocked and prevented from rotating further, and the medical fluid-flow regulating device 100' is irreversibly inactivated. Pivoting of the lever of the blocking unit 40' may be made irreversible in other different ways (not shown), e.g. by a type of male-female engagement with the central body 11 of the rotor or one of the relief structures 18 or by a sort of curved guide where the lever or the protruding bar 35 jumps over an edge of the guide and cannot return back, or by using a clap spring or resilient properties of the lever itself. This is an example of how the blocking unit 40' is displaceable with respect to the rotor 10' above a torque and/or fluidic-pressure threshold value thereby irreversibly engaging with the rotor 10' and preventing the rotor 10' to be rotated.

According to other embodiments, the coupling 30' itself could function as a blocking unit upon displacement or upon deformation above the torque and/or fluidic-pressure threshold value. For example, the connector 33 could be designed to break by twisting above the torque and/or fluidic-pressure threshold value and to act as a blocking unit.

Figure 3A:
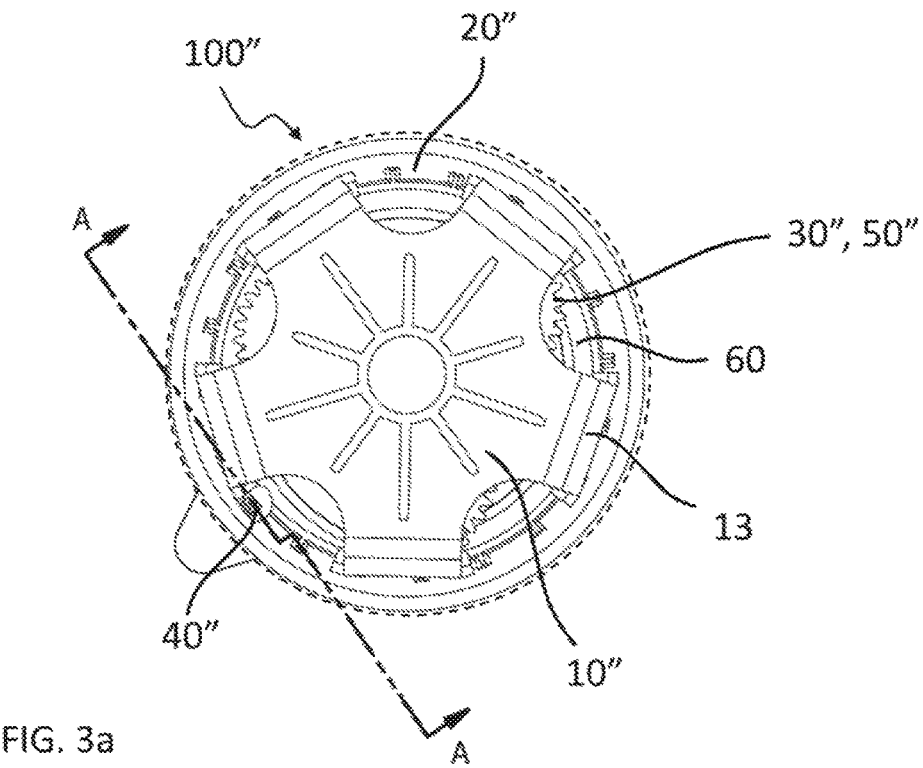
FIG. 3a is a top partial view of a third embodiment of medical fluid-flow regulating device showing only some of the inner components for clarity purpose.
Figure 3B:
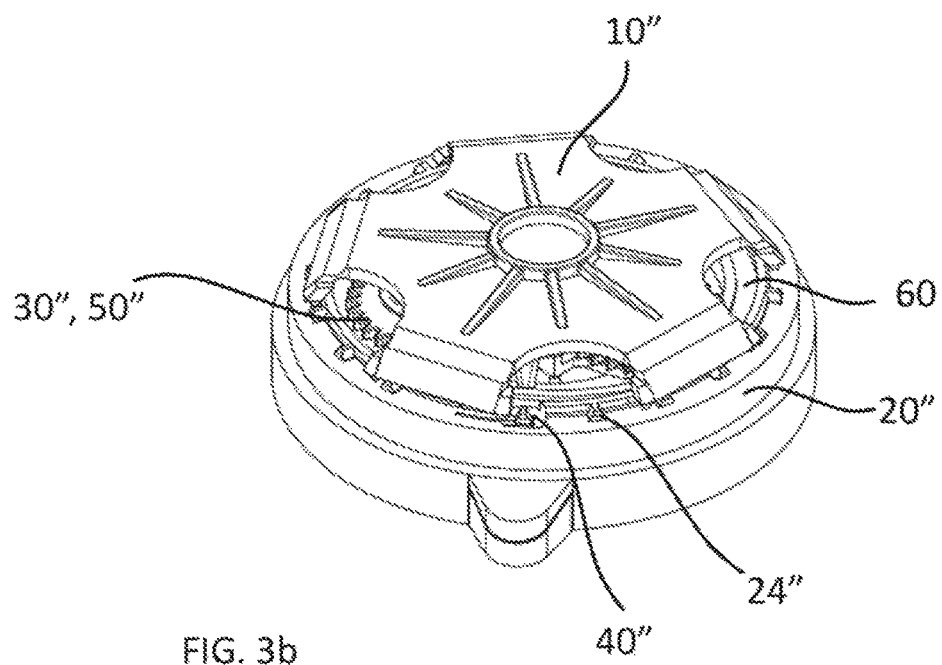

With combined reference to FIG. 3a and FIG. 3b, a third embodiment of medical fluid-flow regulating device 100" is described. The medical fluid-flow regulating device 100" of FIG. 3a-3b comprises a rotor 10" and a flow-regulator element 50" engaged with each other via a coupling 30". The medical fluid-flow regulating device 100" further comprises a safe-lock mechanism 20" and a blocking unit 40".

The flow-regulator element 50" is in this embodiment a peristaltic pump comprising an epicyclical gear system comprising three planet gears 30" arranged about the shaft of the rotor 10", the shaft of the rotor 10" comprising a corresponding gear engaged or engageable with all three planet gears 30" so that upon rotation of the rotor 10" all three planet gears 30" rotate and at the same time revolve about the axis of rotation of the rotor 10". Arranged below each planet gear 30" is pump wheel (not shown) adapted to be in contact with and apply pressure to a tubing 60, at least during part of the revolving. Revolving of the planets gears 30" thus results in peristaltic pumping of a fluid contained in the tubing 60, that is part of a fluidic conduit, and thereby in flow regulation. An example of such a pump system is described in more detail e.g. in EP2674177A1.

The planet gears 30" thus act as coupling between the rotor 10" and the flow-regulator element 50". The rotor 10", apart from the different form of the shaft and way of coupling to the flow-regulator element 50", is similar in form and function to that of FIG. 1a-1f and FIG. 2a-2f.

The safe-lock mechanism 20" is different in form but similar in function to that of FIG. 1a-1f and FIG. 2a-2f. In particular, the safe-lock mechanism 20" is structured as a recessed body fixed with respect to the medical flow-regulating device 100", comprising a bottom and sidewalls forming a chamber in between that is closed on top by the rotor 10". The chamber is adapted to contain the flow-regulator element 50", including the coupling 30", at least part of the fluidic channel 60, and the shaft of the rotor 10". The sidewalls comprise on the upper edge a plurality of protrusions 24" at regular intervals. These protrusions are similar in function to the holes 24 of the safe-lock mechanism 20, 20' of FIG. 1a-1f and FIG. 2a-2f respectively, for locking the rotor 10".

Figure 3C:
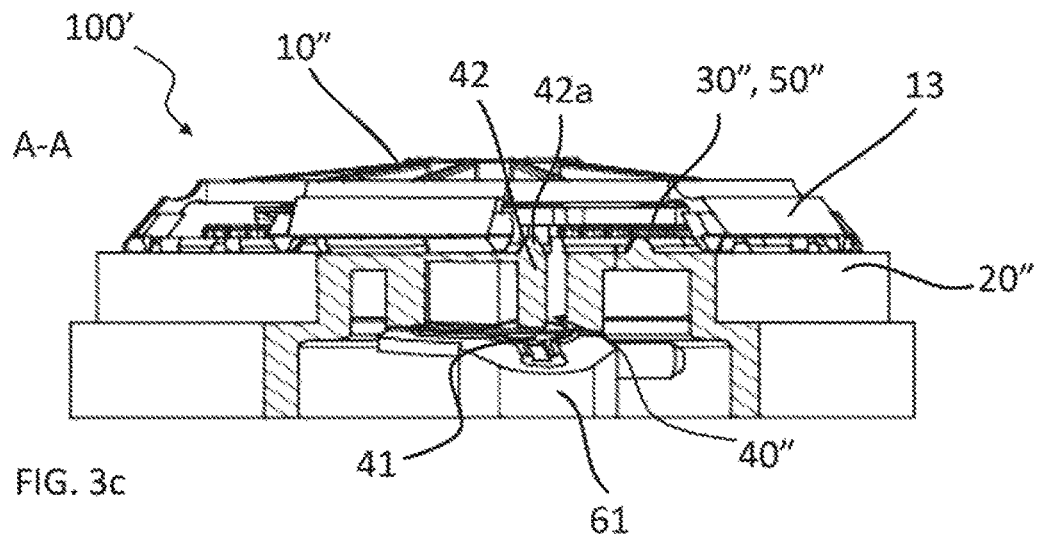
FIG. 3c is a partial cross-sectional view of the medical fluid-flow regulating device as shown in FIG. 3a though line A-A, in a standby condition.
Figure 3D:
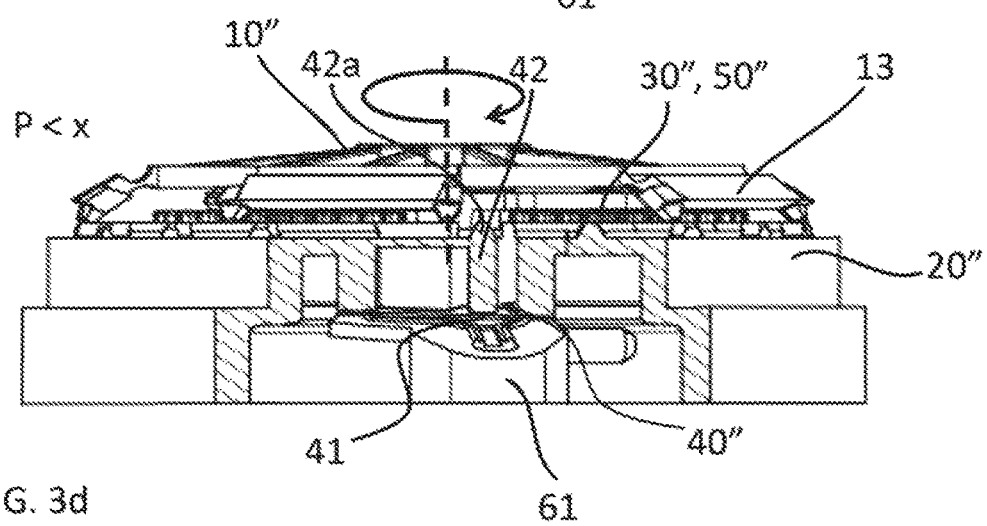
FIG. 3d is a partial cross-sectional view similar to that of FIG. 3c, with the components in an operational condition.
Figure 3E:
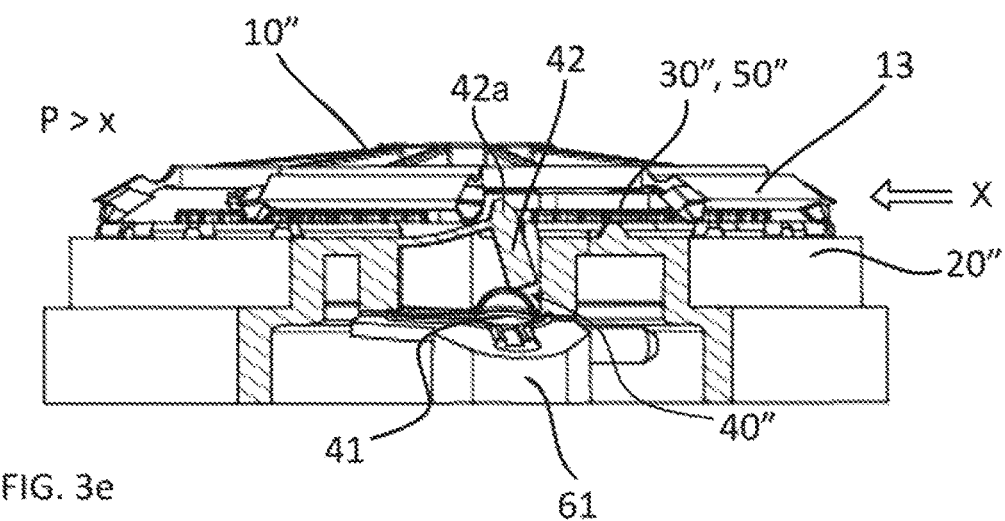
FIG. 3e is a partial cross-sectional view similar to that of FIG. 3c, with the components in an irreversibly inactivated condition.

The blocking unit 40" is better illustrated in FIG. 3c-3e.

The way of operating of the medical fluid-flow-regulating device 100" and in particular of the blocking unit 40" will be now described with reference to FIG. 3c, FIG. 3d, FIG. 3e and FIG. 7.

Figure 7:
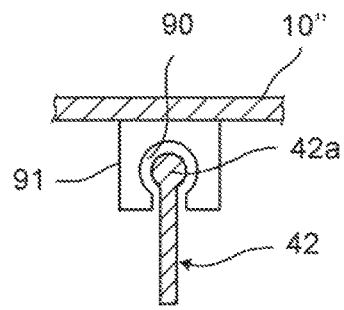
FIG. 7 is a cross-sectional view along the direction X of FIG. 3e of a particular of the irreversible blocking unit in the embodiment shown in FIGS. 3c-3e.

FIG. 3c is a partial cross-sectional view of the medical fluid-flow regulating device 100" through line A-A of FIG. 3a, in a standby condition, in which the rotor 10" is locked by the safe-lock mechanism 20" and unable to rotate. In particular, analogously to the previous embodiments, when fluid flow regulation is not needed, the actionable sections 13 of the rotor 10" are in a rest position and the protrusions 24" of the safe-lock mechanism 20" lock the rotor 10" and prevent that the rotor 10" is accidentally rotated when not needed. In FIG. 3c, the structure and function of the blocking unit 40" can be better appreciated in cross-section. The blocking unit 40" is functionally coupled to a fluidic connector 61, connecting the tubing 60 (not shown in FIG. 3c) to an infusion element (not shown). The fluidic connector 61 comprises a channel (not shown) for the passage of fluid from the tubing 60 to the infusion element. The blocking unit 40" comprises a membrane in fluidic communication with the channel of the fluidic connector 61. The blocking unit 40" further comprises a lever 42 in correspondence to and functionally coupled to the membrane 41 that if pivoted upwards towards the rotor 10" can permanently block the rotor 10". In fact, as shown in FIG. 7, which represents a partial sectional view along the direction X of FIG. 3e, the lever 42 has a bulb-shaped upper end 42a which engages a corresponding bulb-shaped seat 90 located on a supporting element 91 which protrudes downward from the lower side of the rotor 10". The supporting element 91 is made of a flexible material, so that the lever 42 can snap-fit in the seat 90, which prevents the lever 42 from returning back to its lower position. Therefore, the seat 90 forms the irreversible stop element according to this embodiment of the invention.

In the standby condition of FIG. 3c the membrane 41 is in a relaxed condition and the lever 42 is in a non-pivoted position that does not impede rotation of the rotor 10" if unlocked.

FIG. 3d is a partial cross-sectional view similar to that of FIG. 3c and showing the same components in an operational condition. In particular, upon application of a magnetic force provided by an external hand-held activation device (shown in FIG. 4) the actionable sections 13 are stretched above the protrusions 24" of the safe-lock mechanism 20". The rotor 10" is thereby unlocked and capable of being rotated by application of another magnetic force by the same hand-held activation device.

In particular, when the rotor 10" is unlocked and the fluidic pressure P is below a threshold value x (P<x) rotation of the rotor 10" results in revolution of the pump wheels of the flow-regulator element 50" thereby pumping fluid through the tubing 60 (not shown in FIG. 3d) and regulating fluid flow. The membrane 41 of the blocking unit 40" as long as the fluidic pressure P remains below the threshold value x (P<x) remains in a relaxed position or at most in a slightly expanded position, possibly oscillating between a slightly expanded position and a relaxed position, where even in the slightly expanded position the lever 42 remains in a non-pivoted position that does not impede rotation of the rotor 10". In particular, the lever 42 may prevent membrane 41 from expanding.

After flow regulation, e.g. after infusion of a dose of medicament, by rotating the rotor 10" as necessary, the actionable sections 13 are configured to resiliently return to the original rest position upon removal of the hand-held activation device and thereby of the magnetic force, thereby engaging again with the safe-lock mechanism 20" and locking the rotor 10", as illustrated in FIG. 3c.

FIG. 3e is a partial cross-sectional view similar to that of FIG. 3d showing the same components in an irreversibly inactivated condition. In particular, when the fluidic pressure P is above a threshold value x (P>x) for any of the reasons mentioned above, e.g. due to a clogging and fluid cannot be pumped out through the infusion element, when starting to rotate the rotor 10" the membrane 41 of the blocking unit 40" is expanded, overcoming the force applied by the lever 42. As a consequence, the lever 42 is pivoted upwards into engagement with the rotor 10" that is prevented from further rotation. Even in this case, the lever 42 is so designed that this position is irreversible, as described above in an exemplary embodiment, and even if the membrane 41 returns to a relaxed position, the lever 42 remains in a pivoted position thereby irreversibly blocking the rotor 10".

Thus, if the fluidic pressure P is larger than the force required to expand the membrane 41 and to pivot the lever 42, and which defines the threshold value in this case, then the rotor 10" is permanently blocked and prevented to further rotate, and the medical fluid-flow regulating device 100" is irreversibly inactivated. This is an example of how the blocking unit 40" is displaceable with respect to the rotor 10" above a fluidic pressure threshold value thereby irreversibly engaging with the rotor 10" and preventing the rotor 10" to be rotated. In this case, the membrane 41 when expanded blocks the rotor 10" indirectly via the lever 42. However, the membrane 41 could be arranged to block the rotor 10" or any other movable element also directly.

Figure 8A:
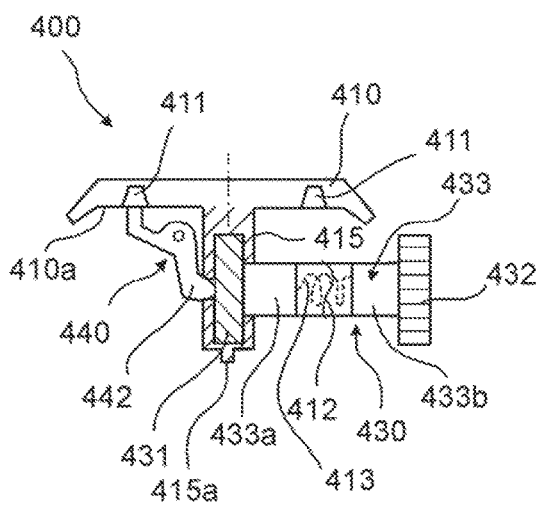
FIG. 8a is a partial cross-sectional view of another embodiment of the medical fluid-flow regulating device, in an operational condition.
Figure 8B:
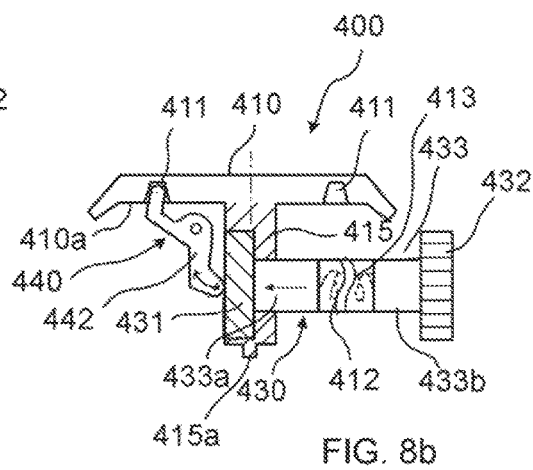
FIG. 8b is a partial cross-sectional view of the embodiment of FIG. 8a, with the components in a particular operational condition.

FIGS. 8a and 8b show a different embodiment of the invention. The medical fluid-flow regulating device 400 comprises a rotor 410 and a flow-regulator element (not shown) engaged with each other via a coupling 430 as described above for the other embodiments. The medical fluid-flow regulating device 400 further comprises a safe-lock mechanism as previously described and a blocking unit 440.

The rotor 410 comprises a downwardly-protruding shaft 415 comprising a spiral groove in the form of a screw thread. The shaft 415 ends inferiorly with a tip 415a that is insertable in a seat (not shown) for supporting its rotation. This seat is positioned on the internal wall of the device housing. The lower side 410a of the rotor 410 comprises a plurality of circumferentially-spaced recesses 411.

The coupling 430 is a gear coupling comprising a first gear wheel 431, a second gear wheel 432 and an extensible connector 433 connecting the first gear wheel 431 to the second gear wheel 432 so that the second gear wheel 432 is rotatable together with the first gear wheel 431. In particular, the first gear wheel 431 has a pitch that matches the thread of the shaft 415 of the rotor 410 and is coupled to the shaft 415 in a manner that, when the rotor 410 rotates, the first gear wheel 431 and therefore also the second gear wheel 432 rotate. The second gear wheel 432 is in turn coupled to a third gear wheel 34 (not shown, the reference number relates to the embodiment of FIGS. 1a-1f that is exactly the same in this respect) operatively coupled to the flow-regulator element 50 as described with reference to the previous embodiments.

The extensible connector 433 comprises a first portion 433a, integral with or connected to the first gear wheel 431, and a second portion 433b, integral with or connected to the second gear wheel 432. The first and the second portions 433a, 433b are coupled through irregularly shaped, matching edges 412, e.g. a sinusoidal profile, so that there is only one matching position allowed. The first and the second portions 433a, 433b of the extensible connector 433 are kept together by a spring 413 (shown in dotted line in the figures) that is fixed in correspondingly facing recesses housed in the said first and second portions 433a, 433b. The spring 413 allows the connector 433 to be extensible.

The blocking unit 440 comprises a lever 442 having a first end proximal to the first gear wheel 431 and a second, upwardly facing end proximal to the lower side of the rotor 410. The lever 442 is hinged in such a way that, upon a pushing force applied to the first end thereof by a longitudinal displacement of the coupling 430, it pivots around its hinge axis.

When, for some of the reasons set forth above, the second gear wheel 432 is blocked, and the torque T is above a threshold value x (T>x), the rotor 410, although unlocked and although energy is being provided to it by the external hand-held activation device for rotating, is unable to cause movement of the flow-regulator element. Because the flow-regulator element cannot move in the axial direction and therefore the gear wheel 432 cannot rotate, the further rotation of the rotor 410 forces the first portion 433a of the extensible connector 433 to rotate and at the same time to advance along a longitudinal direction. This is allowed by the fact that the first and the second portions 433a, 433b of the extensible connector 433 are joined by the spring 413. This movement causes the second end of the lever 442 to raise up to a point where it engages one of the recesses 411 of the rotor 410.

The rotor 410 is therefore irreversibly inactivated and prevented from rotating further. In fact, when the first portion 433a of the extensible connector 433 rotates and advances concomitantly, the matching edges 412 of the two portions 433a, 433b are de-coupled and can no longer find a matching position due to their relative rotation. Therefore, the first portion 433a of the extensible connector 433 cannot return back to the non extended condition and the lever 432 rests permanently engaged in the recesses 411 of the rotor 410. Thus, the matching edges 412 form the irreversible stop element according to this embodiment of the invention.

Figure 9A:
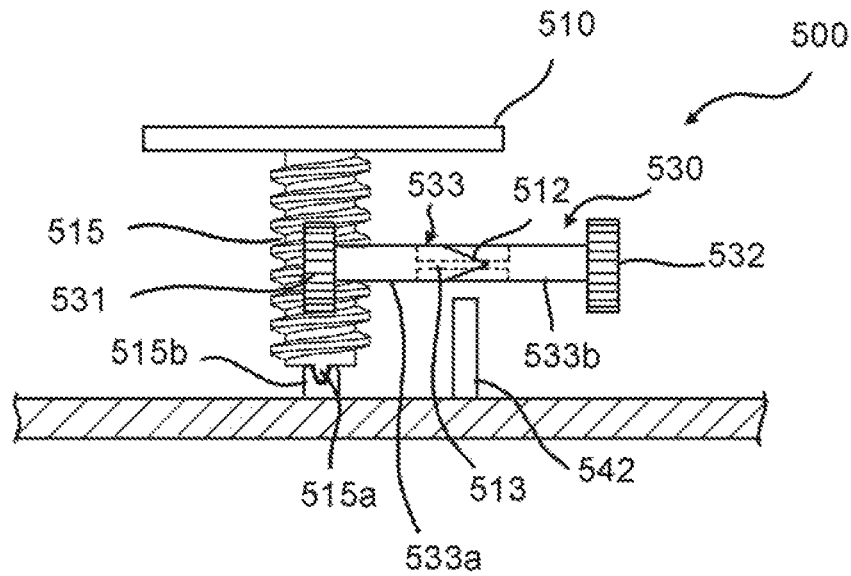
FIGS. 9a and 9b are partial cross-sectional views of another embodiment of the medical fluid-flow regulating device, in two different operational conditions, respectively.
Figure 9B:
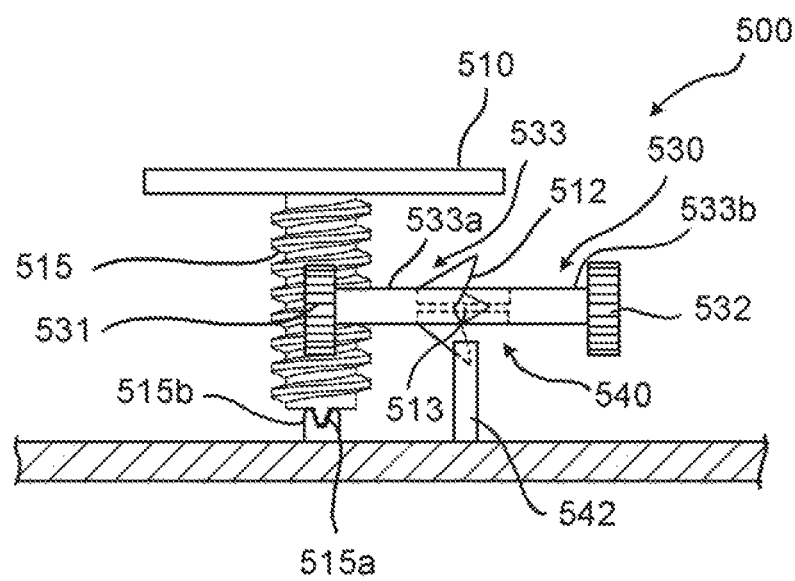

FIGS. 9a and 9b show additional embodiments of the invention. The medical fluid-flow regulating device 500 comprises a rotor 510 and a flow-regulator element (not shown) engaged with each other via a coupling 530 as described above for the other embodiments. The medical fluid-flow regulating device 500 further comprises a safe-lock mechanism as previously described and a blocking unit 540.

The rotor 510 comprises a downwardly-protruding shaft 515 comprising a spiral groove in the form of a screw thread. The shaft 515 ends inferiorly with a tip 515a that is insertable in a seat 515b for supporting its rotation. The seat 515b is positioned on the internal wall of the device housing.

The coupling 530 is a gear coupling comprising a first gear wheel 531, a second gear wheel 532 and a connector 533 connecting the first gear wheel 531 to the second gear wheel 532 so that the second gear wheel 532 is rotatable together with the first gear wheel 531. In particular, the first gear wheel 531 has a pitch that matches the thread of the shaft 515 of the rotor 510 and is coupled to the shaft 515 in a manner that, when the rotor 510 rotates, the first gear wheel 531 and therefore also the second gear wheel 532 rotate. The second gear wheel 532 is in turn coupled to a third gear wheel 34 (not shown, the reference number relates to the embodiment of FIGS. 1a-1f that is exactly the same in this respect) operatively coupled to the flow-regulator element 50 as described with reference to previous embodiments.

The connector 533 comprises a first portion 533a, integral with or connected to the first gear wheel 531, and a second portion 533b, integral with or connected to the second gear wheel 532. The first and the second portions 533a, 533b are coupled through irregularly shaped, matching edges 512, e.g. a zig-zag profile, so that there is only one matching position allowed. Moreover, at least one of said portions 533a, 533b is made, totally or in part of a flexible material. If only part of the said at least one portion is made of a flexible material, this part comprises the edge 512.

The first and the second portions 533a, 533b of the connector 533 are rotatably kept together by a hinged bar 513 (shown in dotted line in the figures) that is hinged in correspondingly facing recesses housed in the said first and second portions 533a, 533b. In another embodiment, the hinged bar 513 may be replaced by a spring, as in the embodiment of FIGS. 8a and 8b, to make the connector 533 extensible.

The blocking unit 540 comprises an upwardly-protruding tooth 542 which is fixed on the internal wall of the device housing.

When, for some of the reasons set forth above, the second gear wheel 532 is blocked and the torque T is above a threshold value x (T>x), the rotor 510, although unlocked and although energy is being provided to it by the external hand-held activation device for rotating, is unable to cause movement of the flow-regulator element. Because the flow-regulator element cannot move in the axial direction and therefore the gear wheel 532 cannot rotate, the further rotation of the rotor 510 forces the first portion 533a of the connector 533 to rotate and therefore to displace the matching edges 512. This is allowed by the fact that the first and the second portions 533a, 533b of the connector 533 are joined by the hinged bar 513. When the matching edge 512 of the first portion 533a is displaced by rotation, it opens like the petals of a flower (see FIG. 9b). In this way, the open edge 512 interferes with the tooth 542, thus blocking the first gear wheel 531 and concurrently also the rotor 510.

The rotor 510 is therefore irreversibly inactivated and prevented from rotating further. In fact, when the first portion 533a of the connector 533 rotates, the matching edges 512 of the two portions 533a, 533b are de-coupled and can no longer find a matching position due to their relative rotation. Therefore, the open edge 512 of the first portion 533a cannot be returned to its closed condition, causing the blocking of the rotor 510 to be irreversible. Thus, the matching edges 512 form the irreversible stop element according to this embodiment of the invention.

Figure 10A:
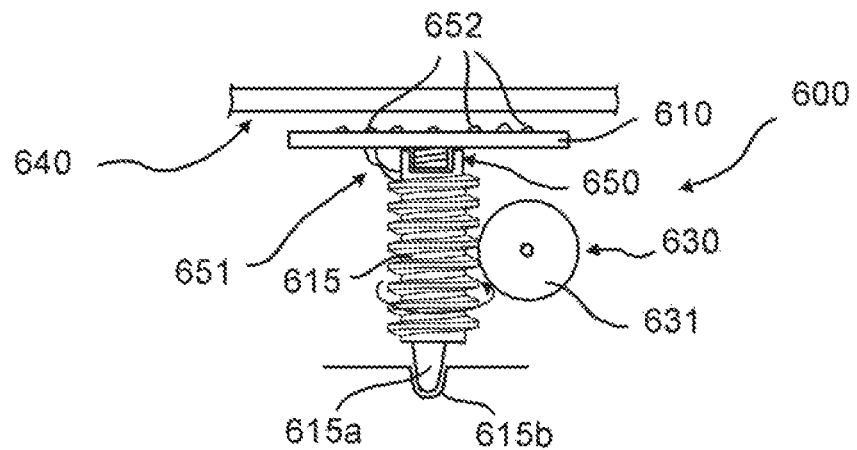
FIGS. 10a and 10b are partial cross-sectional views of another embodiment of the medical fluid-flow regulating device, in two different operational conditions, respectively.
Figure 10B:
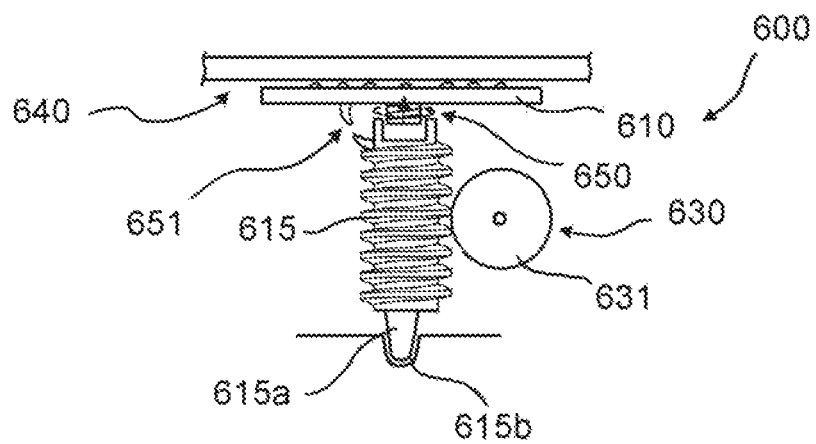

FIGS. 10a and 10b show additional embodiments of the invention. The medical fluid-flow regulating device 600 comprises a rotor 610 and a flow-regulator element (not shown) engaged with each other via a coupling 630 as described above for the other embodiments. The medical fluid-flow regulating device 600 further comprises a safe-lock mechanism as previously described and a blocking unit 640.

The rotor 610 comprises a downwardly-protruding shaft 615 comprising a spiral groove in the form of a screw thread. The shaft 615 ends inferiorly with a tip 615a that is insertable in a seat 615b for supporting its rotation. The seat 615b is positioned on the internal wall of the device housing.

More precisely, the rotor 610 is coupled to the shaft 615 by means of a screw connector 650. The screw connector 650 comprises a screw extending downwardly from the rotor 610 and a longitudinal threaded hole in the upper portion of the shaft 615. Moreover, the shaft 615 and the rotor 610 are fixed together by a tongue 651 linking the lower side of rotor 610 with the shaft 615 surface. This tongue 651 has a predetermined breaking strength in order to break if the torque T is above a threshold value x (T>x).

The rotor 610 further comprises on its top side a plurality of protrusions 652.

The coupling 630 is a gear coupling comprising a first gear wheel 631, a second gear wheel and a connector connecting the first gear wheel 631 to the second gear wheel so that the second gear wheel is rotatable together with the first gear wheel 631. The second gear wheel and the connector are not shown in FIGS. 10a-10b as they represent longitudinal views with respect to this element, but they are identical to the coupling 30 in FIGS. 1a-1f. In particular, the first gear wheel 631 has a pitch that matches the thread of the shaft 615 of the rotor 610 and is coupled to the shaft 615 in a manner that, when the rotor 610 rotates, the first gear wheel 631 and as a result the second gear wheel also rotates. The second gear wheel is in turn coupled to a third gear wheel (also not shown, but identical to the embodiment of FIGS. 1a-1f) operatively coupled to the flow-regulator element as described with reference to the previous embodiments.

When, for some of the reasons set forth above, the flow-regulator element and thus also the coupling are blocked and the torque T is above a threshold value x (T>x), the rotor 610, although unlocked and although energy is being provided to it by the external hand-held activation device for rotating, is unable to cause movement of the flow-regulator element. Because the flow-regulator element cannot move in the axial direction and therefore the second gear wheel cannot rotate, the further rotation of the rotor 610 causes the tongue 651 to be broken. The rotor 610 is thus free to rotate with respect to the shaft 615, which is blocked by the coupling 630. This causes the rotor 610 to unscrew from the shaft 615 and to raise as shown in FIG. 10b. In this way the rotor 610, in particular the protrusions 652, come into contact with the internal wall of the device housing, that stops the rotation of the rotor 610 by friction. Alternatively, the internal surface of the device housing can on its turn comprise a number of protrusions that may interfere with the protrusions 652 of the rotor 610. The rotor 610 is therefore irreversibly inactivated and prevented from rotating further. Thus, the protrusions 652 form the irreversible stop element according to these embodiments of the invention.

Figure 11A:
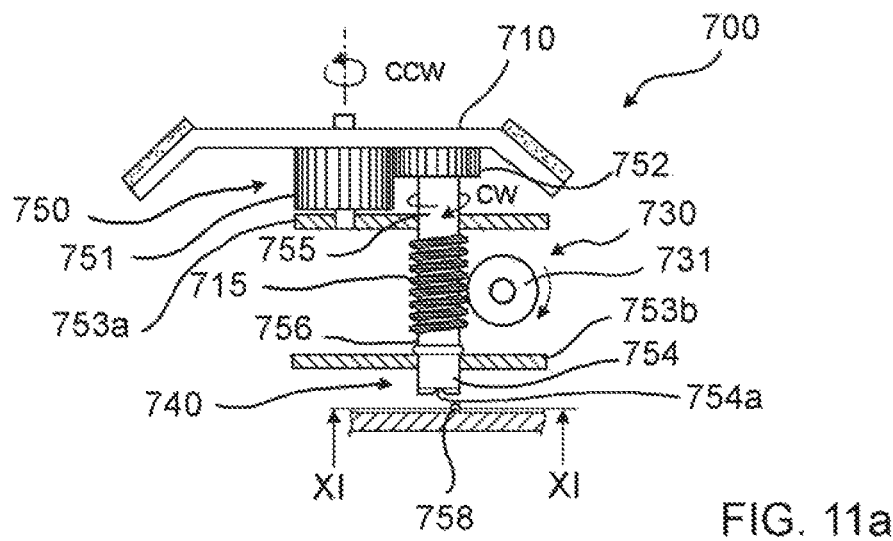
FIGS. 11a and 11b are partial cross-sectional views of a further embodiment of the medical fluid-flow regulating device, in two different operational conditions, respectively.
Figure 11B:
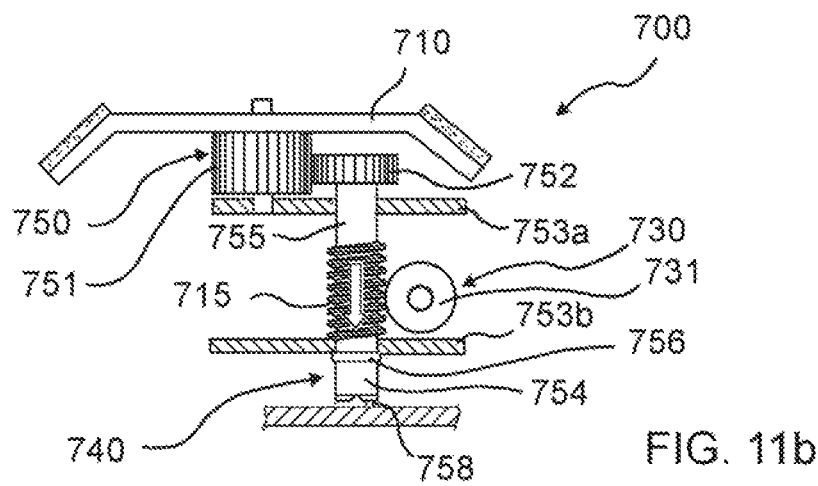

FIGS. 11a and 11b show further embodiments of the invention. The medical fluid-flow regulating device 700 comprises a rotor 710 and a flow-regulator element (not shown) engaged with each other via a coupling 730 as described above for the other embodiments. The medical fluid-flow regulating device 700 further comprises a safe-lock mechanism as previously described and a blocking unit 740.

The rotor 710 comprises a downwardly-protruding shaft 715 comprising a spiral groove in the form of a screw thread. The rotor 710 is coupled to the shaft 715 by means of a gear coupling 750 comprising a rotor gear 751 and a shaft gear 752. The rotor gear 751 rotates integrally with the rotor 710 and it is inferiorly hinged to a first support element 753a fixed on the device housing.

The shaft gear 752 is positioned at the top end of the shaft 715, to which it is linked by a rod portion 755 passing through a hole in the first support element 753a which functions as a guiding element.

Figure 12:
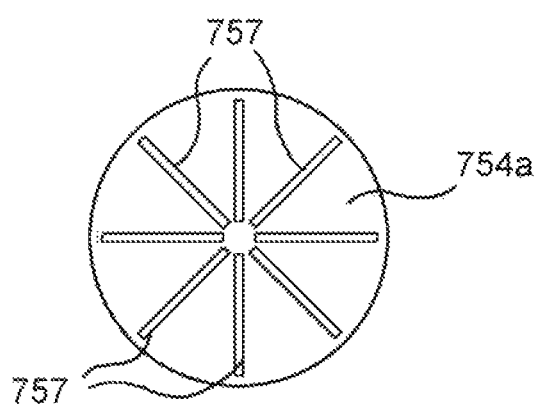
FIG. 12 is a planar view along direction XI-XI of FIG. 11a of a particular of the device of FIGS. 11a-11b.

The shaft 715 ends inferiorly with a not-threaded portion 754 passing through a hole in a second support element 753b fixed to the device housing. The not-threaded portion 754 of the shaft 715 comprises an annular rib 756 that, in a normal operational condition (see FIG. 11a) is located above the second support element 753b. The annular rib 756 is made of a flexible material that can deform by application of a predetermined downward force. Moreover, the not-threaded portion 754 comprises a ribbed bottom surface 754a (see FIG. 12) comprising a plurality of ribs 757.

The coupling 730 is a gear coupling comprising a first gear wheel 731, a second gear wheel and a connector connecting the first gear wheel 731 to the second gear wheel so that the second gear wheel is rotatable together with the first gear wheel 731. The second gear wheel and the connector are not shown in FIGS. 11a-11b as they represent longitudinal views with respect to this element, but they are identical to the coupling 30 in FIGS. 1a-1f. In particular, the first gear wheel 731 has a pitch that matches the thread of the shaft 715 and is coupled to the shaft 715 in a manner that, when the rotor 710 rotates, the first gear wheel 731 and therefore also the second gear wheel rotate. The second gear wheel is in turn coupled to a third gear wheel (also not shown, but identical to the embodiment of FIGS. 1a-1f) operatively coupled to the flow-regulator element as described with reference to the previous embodiments.

When, for some of the reasons set forth above, the flow-regulator element and thus also the coupling are blocked and the torque T is above a threshold value x (T>x), the rotor 710, although unlocked and although energy is being provided to it by the external hand-held activation device for rotating, is unable to cause movement of the flow-regulator element. Because the flow-regulator element cannot move in the axial direction and therefore the second gear wheel cannot rotate, the rotation of the rotor 710 coupled to the shaft 715 causes the rotation of this latter. As the coupling 730 is blocked, the shaft 715 is caused to screw by interference with the blocked first gear wheel 731 and thus to move downward (see FIG. 11b). As the torque is above the said threshold value x, the downward force overcomes the compressive strength of the annular rib 756, which snaps below the second support element 753b. In its movement downward, the bottom surface 754b of the shaft 715 touches the wall of the device housing and by interference, e.g. friction, with it the shaft 715 and the rotor 710 are blocked. The internal wall of the device housing also may comprise a toothed profile 758 to better interfere with the ribs 757 of the shaft 715.

The rotor 710 is therefore irreversibly inactivated and prevented from rotating further. In fact, the annular rib 756 of the not-threaded portion 754 of the shaft 715 is unable to snap above the second support element 753b even if the rotor 710 is freely rotated in the other direction, as the annular rib 756 is designed to not deform when the torque is lower than the said threshold value x. Thus, the annular rib 756 together with the ribbed bottom surface 754a of the shaft 715 form the irreversible stop element according to the invention meaning.

Although in the above examples, the blocking unit 40, 40', 40", 140, 240, 340, 440, 540, 640, 740 was described as a rotor blocking unit, it can be easily adapted as a blocking unit for any movable component of the medical fluid-flow regulating device 100, 100', 100", including and not limited to any element of the coupling 30, 30', 30", any element of the fluid flow regulator 50, 50", as long an increase in the torque and/or fluidic pressure above a threshold value results in irreversible prevention of movement or of further movement of any one or more of the above movable components and thereby in irreversible inactivation of the medical fluid-flow regulating device 100, 100', 100". Also, the presence of a safe-lock mechanism 20, 20', 20" is entirely optional, although the combination of both a safe-lock mechanism and a blocking unit synergistically increases the degree of security of the medical fluid-flow regulating device, by ensuring that the medical fluid-flow regulating device cannot be used when its proper operation is impeded and also that flow regulation does not occur when the medical fluid-flow regulating device can operate properly but flow regulation is not needed. Also different kinds of safe-lock mechanisms can be designed than the ones depicted, e.g. as disclosed in EP2379132. Moreover, although only one kind of rotor 10, 10', 10" was shown in the examples, other kinds of rotors may be employed as well, for example a ratchet-like rotor rotatable stepwise in one direction by alternated turning of a wrench about a pivotal axis between a first position and a second position, e.g. by applying an alternated magnetic field, e.g. as disclosed in EP2674177A1.

FIG. 4 shows schematically a system 300 comprising a medical fluid-flow regulating device 100, 100', 100" and a hand-held activation device 200 in an energy-transfer position. The hand-held activation device 200 is separate from the medical fluid-flow regulating device 100, 100', 100". The hand-held activation device 200 comprises a drive unit 220 that in this case is also an unlocking unit and herein referred to as an unlocking/drive unit 220. In particular, the unlocking/drive unit 220 comprises a magnetic field source, capable of generating a magnetic force acting at the same time radially outwards and symmetrically on all actionable sections 13 of the rotor 10, 10', 10", 410, 510, 610, 710. In the absence of the hand-held activation device 200, i.e. when the hand-held activation device 200 and the medical fluid-flow regulating device 100, 100', 100", 400, 500, 600, 700 are not in the energy transfer position, the actionable sections 13 are in the rest position and are engaged with the safe-lock mechanism 20, 20', 20". The rotor 10, 10', 10", 410, 510, 610, 710 is thus locked and prevented from rotating. The medical fluid-flow regulating device 100, 100', 100", 400, 500, 600, 700 is therefore in a standby condition. The rotor 10, 10', 10", 410, 510, 610, 710 is unlockable and rotatable by temporarily docking the hand-held activation device 200 to the medical fluid-flow regulating device 100, 100', 100", 400, 500, 600, 700 in an energy transfer position, which enables the unlocking/drive unit 220 to transfer the energy required to move the actionable sections 13 to the stretched positions thereby unlocking the rotor 10, 10', 10", 410, 510, 610, 710 and the energy required for rotating the unlocked rotor 10, 10', 10", 410, 510, 610, 710. Rotation of the rotor 10, 10', 10", 410, 510, 610, 710 results in transfer of moving force from the rotor 10, 10', 10", 410, 510, 610, 710 to the fluid-flow regulating element 50, 50", via the coupling 30, 30', 30", 430, 530, 630, 730 and thereby in fluid-flow regulation. The unlocking/drive unit 220 has thus the double function of unlocking the rotor 10, 10', 10", 410, 510, 610, 710 and driving the rotor 10, 10', 10", 410, 510, 610, 710 after unlocking it. The rotor 10, 10', 10", 410, 510, 610, 710 is again lockable by removing the hand-held activation device 200 from the energy-transfer position, thus removing the source of energy, which keeps the actionable sections 13 in the stretched positions, and allowing the actionable sections 13 to return to the rest positions in engagement with the safe-lock mechanism 20, 20', 20".

Medical fluid-flow regulating devices 100, 100', 100', 400, 500, 600, 700 are in this example medical infusion devices comprising an infusion element 70 for infusion a fluid medicament upon flow regulation.

The system 300 further comprises a sensor 210 for detecting rotation of the rotor 10, 10', 10", 410, 510, 610, 710.

The sensor 210 comprises a first sensor component 211 in the medical fluid-flow regulating device 100, 100', 100", 400, 500, 600, 700, adapted to be detected by a second sensor component 212 in the hand-held activation device 200. According to certain embodiments the first sensor component 211 comprises at least one magnet and the second sensor component 212 is a Hall effect sensor.

The hand-held activation device 200 further comprises a controller 250 programmed to control, based on information provided by the sensor 210, if rotation of the rotor 10, 10', 10", 410, 510, 610, 710 fails despite operation of the unlocking/drive unit 220 for rotating the rotor 10, 10', 10", 410, 510, 610, 710 and/or if operation of the unlocking/drive unit 220 corresponds to intended rotation of the rotor 10, 10', 10", 410, 510, 610, 710, in other words if the energy provided for rotating the rotor 10, 10', 10", 410, 510, 610, 710 was in fact transferred to the rotor 10, 10', 10", 410, 510, 610, 710 and transformed into rotation of the rotor 10, 10', 10", 410, 510, 610, 710 as intended.

The controller 250 is programmed to interpret failure of detection of rotation of the rotor 10, 10', 10", 410, 510, 610, 710 as an increase of the torque and/or of the fluidic pressure above the threshold value and to associate it to a condition of irreversible inactivation of the fluid-flow regulating device 100, 100', 100", 400, 500, 600, 700.

The controller 250 may be programmed to warn and/or to stop or prevent operation of the unlocking/drive unit 220 and/or prevent further use of the fluid-flow regulating device 100, 100', 100", 400, 500, 600, 700 if detection of rotation of the rotor 10, 10', 10", 410, 510, 610, 710 fails. The hand-held device 200 comprises for example a display 270 on which a warning signal may be displayed, and which may be accompanied by a recognizable acoustic or vibrational signal.

The hand-held activation device 200 may have other functions, e.g. functions of control, feedback and interface functions, such as e.g. disclosed in EP2617445 and not further elucidated here.

With continued reference to FIG. 4, a method of detecting irreversible inactivation of the medical fluid-flow regulating device 100, 100', 100", 400, 500, 600, 700 is also described. The method comprises detecting if the rotor fails to rotate despite operation of the unlocking/drive unit 220 for rotating the rotor 10, 10', 10", 410, 510, 610, 710. The method further comprises warning and/or stopping operation of the drive unit and/or preventing further use of the fluid-flow regulating device 100, 100', 100", 400, 500, 600, 700 if detection of rotation of the rotor 10, 10', 10", 410, 510, 610, 710 fails. Of course numerous variations of the described embodiments are possible without departing from the spirit and scope of the claimed invention.

What is claimed is:

1. A medical fluid-flow regulating device comprising a rotor and a flow-regulator element engaged or engageable with each other via a coupling that below a torque and/or fluidic-pressure threshold value allows the flow-regulator element to move upon rotation of the rotor and thereby regulate fluid flow and also comprising a blocking unit that above the torque and/or fluidic-pressure threshold value irreversibly blocks the rotor or the flow-regulator element or the coupling between the rotor and the flow-regulator element.

2. The medical fluid-flow regulating device of claim 1 wherein above the torque and/or the fluidic pressure threshold value, any one or more of the rotor, the flow-regulator element, the coupling, the blocking unit or any elements thereof are displaceable with respect to each other resulting in irreversible engagement with the blocking unit and in permanent inactivation of the medical fluid-flow regulating device.

3. The medical fluid-flow regulating device of claim 2 wherein the rotor is displaceable with respect to the blocking unit above the torque and/or fluidic-pressure threshold value thereby irreversibly engaging with the blocking unit, and preventing the rotor from rotating.

4. The medical fluid-flow regulating device of claim 2 wherein the blocking unit or any element thereof is displaceable with respect to the rotor above the torque and/or fluidic-pressure threshold value thereby irreversibly engaging with the rotor and preventing the rotor from rotating.

5. The medical fluid-flow regulating device of claim 4 wherein the blocking unit comprises a membrane that above the fluidic-pressure threshold value is expanded such as to directly or indirectly block the rotor and prevent the rotor from rotating.

6. The medical fluid-flow regulating device of claim 2 wherein the flow-regulator element or the coupling between the rotor and the flow-regulator element is displaceable with respect to the rotor or is deformable above the torque and/or fluidic-pressure threshold value thereby functioning as a blocking unit for the rotor or is adapted to move the blocking unit into engagement with the rotor.

7. The medical fluid-flow regulating device of claim 1 wherein the coupling is a gear coupling.

8. The medical fluid-flow regulating device of claim 1 wherein the flow-regulator element is an axial pump element.

9. The medical fluid-flow regulating device of claim 8 wherein the axial pump element is a push or pull element or is coupled to a plunger or piston that is coupled or couplable to a syringe-like or cartridge-like fluid reservoir.

10. The medical fluid-flow regulating device of claim 1, wherein the blocking unit comprises an irreversible stop element that impedes the rotor from rotating again after the blocking unit has blocked it.

11. A system comprising a medical fluid-flow regulating device of claim 1 and a hand-held activation device separate from the medical fluid-flow regulating device, the activation device comprising a drive unit for magnetically or inductively rotating the rotor of the medical fluid-flow regulating device and a sensor for detecting rotation of the rotor.

12. The system of claim 11 wherein the hand-held activation device further comprises a controller programmed to control, based on information from the sensor, if rotation of the rotor fails despite operation of the drive unit for rotating the rotor and/or if operation of the drive unit corresponds to intended rotation of the rotor.

13. The system of claim 12 wherein the controller is programmed to interpret failure of detection of rotation of the rotor as an increase of the torque and or/force and/or of the fluidic pressure above the threshold value and to associate it to a condition of irreversible inactivation of the medical fluid-flow regulating device.

14. The system of claim 12 wherein the controller is programmed to warn and/or to stop or prevent operation of the drive unit and/or prevent further use of the medical fluid-flow regulating device if detection of rotation of the rotor fails.

15. A method of detecting irreversible inactivation of a medical fluid-flow regulating device of claim 1 comprising detecting if the rotor fails to rotate despite operation of a drive unit for rotating the rotor in an energy-transfer position.

16. The method of claim 15 further comprising warning and/or stopping operation of the drive unit and/or preventing further use of the fluid-flow regulating device if detection of rotation of the rotor fails.

* * * * *